US009717533B2

(12) United States Patent
Jackson et al.

(10) Patent No.: US 9,717,533 B2
(45) Date of Patent: Aug. 1, 2017

(54) BONE ANCHOR CLOSURE PIVOT-SPLAY CONTROL FLANGE FORM GUIDE AND ADVANCEMENT STRUCTURE

(71) Applicant: Roger P. Jackson, Prairie Village, KS (US)

(72) Inventors: Roger P Jackson, Prairie Village, KS (US); James L Surber, Kansas City, KS (US)

(73) Assignee: Roger P. Jackson, Prairie Village, KS (US)

( * ) Notice: Subject to any disclaimer, the term of this patent is extended or adjusted under 35 U.S.C. 154(b) by 0 days.

(21) Appl. No.: 14/581,165

(22) Filed: Dec. 23, 2014

(65) Prior Publication Data

US 2016/0022320 A1     Jan. 28, 2016

Related U.S. Application Data

(63) Continuation-in-part of application No. 14/569,142, filed on Dec. 12, 2014.

(60) Provisional application No. 61/920,033, filed on Dec. 23, 2013, provisional application No. 61/915,085, filed on Dec. 12, 2013.

(51) Int. Cl.
*A61B 17/56* (2006.01)
*A61B 17/70* (2006.01)

(52) U.S. Cl.
CPC ................. *A61B 17/7032* (2013.01)

(58) Field of Classification Search
CPC ............ A61B 17/8685; A61B 17/7032
USPC ........................................ 606/270
See application file for complete search history.

(56) References Cited

U.S. PATENT DOCUMENTS

| | | |
|---|---|---|
| 154,864 A | 9/1874 | Harvey |
| 791,548 A | 6/1905 | Fischer |
| 1,300,275 A | 4/1919 | Johnson |
| 1,330,673 A | 2/1920 | Anderson |
| 1,472,464 A | 10/1923 | Ellison |
| 2,005,348 A | 6/1935 | Michell |
| 2,083,092 A | 6/1937 | Richer |
| 2,201,087 A | 5/1940 | Hallowell |
| 2,239,352 A | 4/1941 | Cherry |
| 2,243,717 A | 5/1941 | Moreira |
| 2,295,314 A | 9/1942 | Whitney |
| 2,346,346 A | 4/1944 | Anderson |
| 2,362,999 A | 11/1944 | Elmer |
| 2,445,978 A | 7/1948 | Stellin |
| 2,531,892 A | 11/1950 | Reese |
| 2,532,815 A | 12/1950 | Kindsvatter et al. |
| 2,537,029 A | 1/1951 | Cambern |

(Continued)

FOREIGN PATENT DOCUMENTS

| | | |
|---|---|---|
| AU | 2012203959 | 8/2012 |
| CA | 2268513 | 4/1999 |

(Continued)

OTHER PUBLICATIONS

Brochure of Tyco/Healthcare/Surgical Dynamics on Spiral Radius 90D, Publication Date: Sep. 2001, pp. 1-8.

(Continued)

*Primary Examiner* — Jan Christopher Merene
(74) *Attorney, Agent, or Firm* — Polsinelli PC

(57) ABSTRACT

Open implant closure structures include a helically wound guide and advancement flange form having pivot-splay accommodating and splay control surfaces with opposing load flanks in initial non-parallel relation.

1 Claim, 9 Drawing Sheets

(56) References Cited

U.S. PATENT DOCUMENTS

| | | |
|---|---|---|
| 2,553,337 A | 5/1951 | Shafer |
| 2,778,265 A | 1/1957 | Brown |
| 2,813,450 A | 11/1957 | Dzus |
| 2,833,325 A | 5/1958 | Laisy |
| 2,877,681 A | 3/1959 | Brown |
| 2,927,332 A | 3/1960 | Moore |
| 2,969,250 A | 1/1961 | Kull |
| 3,013,244 A | 12/1961 | Rudy |
| 3,143,029 A | 8/1964 | Brown |
| D200,217 S | 2/1965 | Curtiss |
| 3,236,275 A | 2/1966 | Smith |
| 3,370,341 A | 2/1968 | Allsop |
| 3,444,775 A | 5/1969 | Hills |
| 3,498,174 A | 3/1970 | Schuster et al. |
| 3,584,667 A | 6/1971 | Reiland |
| 3,604,487 A | 9/1971 | Gilbert |
| 3,640,416 A | 2/1972 | Temple |
| 3,812,757 A | 5/1974 | Reiland |
| 3,963,322 A | 6/1976 | Gryctko |
| 3,989,284 A | 11/1976 | Blose |
| 3,997,138 A | 12/1976 | Crock et al. |
| 4,013,071 A | 3/1977 | Rosenberg |
| 4,033,139 A | 7/1977 | Frederick |
| 4,041,939 A | 8/1977 | Hall |
| 4,103,422 A | 8/1978 | Weiss et al. |
| 4,176,679 A | 12/1979 | Roger |
| 4,190,091 A | 2/1980 | Colognori |
| 4,269,246 A | 5/1981 | Larson et al. |
| 4,323,326 A | 4/1982 | Okada et al. |
| 4,347,845 A | 9/1982 | Mayfield |
| 4,369,769 A | 1/1983 | Edwards |
| 4,373,754 A | 2/1983 | Bollfrass et al. |
| 4,409,968 A | 10/1983 | Drummond |
| 4,448,191 A | 5/1984 | Rodnyansky et al. |
| 4,484,570 A | 11/1984 | Sutter et al. |
| 4,492,500 A | 1/1985 | Ewing |
| 4,506,917 A | 3/1985 | Hansen |
| 4,577,448 A | 3/1986 | Howorth |
| 4,600,224 A | 7/1986 | Blose |
| 4,600,225 A | 7/1986 | Blose |
| 4,641,636 A | 2/1987 | Cotrel |
| 4,653,481 A | 3/1987 | Howland et al. |
| 4,653,486 A | 3/1987 | Coker |
| 4,703,954 A | 11/1987 | Ortloff et al. |
| 4,707,001 A | 11/1987 | Johnson |
| 4,743,260 A | 5/1988 | Burton |
| 4,748,260 A | 5/1988 | Marlett |
| 4,759,672 A | 7/1988 | Nilsen et al. |
| 4,763,644 A | 8/1988 | Webb |
| 4,764,068 A | 8/1988 | Crispell |
| 4,790,297 A | 12/1988 | Luque |
| 4,805,602 A | 2/1989 | Puno et al. |
| 4,815,453 A | 3/1989 | Cotrel |
| 4,836,196 A | 6/1989 | Park et al. |
| 4,838,264 A | 6/1989 | Bremer et al. |
| 4,850,775 A | 7/1989 | Lee et al. |
| 4,877,020 A | 10/1989 | Vich |
| 4,887,596 A | 12/1989 | Sherman |
| 4,917,606 A | 4/1990 | Miller |
| 4,946,458 A | 8/1990 | Harms et al. |
| 4,950,269 A | 8/1990 | Gaines, Jr. |
| 4,961,740 A | 10/1990 | Ray et al. |
| 5,005,562 A | 4/1991 | Cotrel |
| 5,019,080 A | 5/1991 | Hemer |
| 5,022,791 A | 6/1991 | Isler |
| 5,034,011 A | 7/1991 | Howland |
| 5,042,982 A | 8/1991 | Harms et al. |
| 5,056,492 A | 10/1991 | Banse |
| 5,067,428 A | 11/1991 | Dickerson et al. |
| 5,067,955 A | 11/1991 | Cotrel |
| 5,073,074 A | 12/1991 | Corrigan et al. |
| 5,084,048 A | 1/1992 | Jacob et al. |
| 5,092,635 A | 3/1992 | DeLange et al. |
| 5,102,412 A | 4/1992 | Rogozinski |
| 5,129,388 A | 7/1992 | Vignaud et al. |
| 5,129,899 A | 7/1992 | Small et al. |
| 5,147,360 A | 9/1992 | Dubousset |
| 5,147,363 A | 9/1992 | Harle |
| 5,154,719 A | 10/1992 | Cotrel |
| 5,176,483 A | 1/1993 | Baumann et al. |
| 5,176,678 A | 1/1993 | Tsou |
| 5,176,680 A | 1/1993 | Vignaud et al. |
| 5,180,393 A | 1/1993 | Commarmond |
| 5,201,734 A | 4/1993 | Cozad et al. |
| 5,207,678 A | 5/1993 | Harms et al. |
| 5,217,497 A | 6/1993 | Mehdian |
| 5,224,596 A | 7/1993 | Kruger |
| 5,234,430 A | 8/1993 | Huebner |
| 5,257,993 A | 11/1993 | Asher et al. |
| 5,261,907 A | 11/1993 | Vignaud et al. |
| 5,263,953 A | 11/1993 | Bagby |
| 5,275,601 A | 1/1994 | Gogolewski et al. |
| 5,282,707 A | 2/1994 | Palm |
| 5,282,862 A | 2/1994 | Baker et al. |
| 5,282,863 A | 2/1994 | Burton |
| 5,306,275 A | 4/1994 | Bryan |
| 5,312,404 A | 5/1994 | Asher et al. |
| 5,321,901 A | 6/1994 | Kelly |
| 5,330,472 A | 7/1994 | Metz-Stavenhagen |
| 5,334,203 A | 8/1994 | Wagner |
| 5,346,493 A | 9/1994 | Stahurski et al. |
| 5,354,292 A | 10/1994 | Braeuer et al. |
| 5,354,299 A | 10/1994 | Coleman |
| 5,358,289 A | 10/1994 | Banker et al. |
| 5,360,431 A | 11/1994 | Puno et al. |
| 5,364,400 A | 11/1994 | Rego, Jr. et al. |
| 5,375,823 A | 12/1994 | Navas |
| 5,382,248 A | 1/1995 | Jacobson et al. |
| 5,385,583 A | 1/1995 | Cotrel |
| 5,387,211 A | 2/1995 | Saadatmanesh et al. |
| 5,387,212 A | 2/1995 | Yuan et al. |
| 5,395,371 A | 3/1995 | Miller et al. |
| 5,409,488 A | 4/1995 | Ulrich |
| 5,409,489 A | 4/1995 | Sioufi |
| 5,415,661 A | 5/1995 | Holmes |
| 5,423,816 A | 6/1995 | Lin |
| 5,427,418 A | 6/1995 | Watts |
| 5,429,639 A | 7/1995 | Judet |
| 5,434,001 A | 7/1995 | Yamada et al. |
| 5,443,467 A | 8/1995 | Biedermann et al. |
| 5,466,237 A | 11/1995 | Byrd, III et al. |
| 5,466,238 A | 11/1995 | Lin |
| 5,468,241 A | 11/1995 | Metz-Stavenhagen et al. |
| 5,474,551 A | 12/1995 | Finn et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,480,401 A | 1/1996 | Navas |
| 5,484,440 A | 1/1996 | Allard |
| 5,487,742 A | 1/1996 | Cotrel |
| 5,489,307 A | 2/1996 | Kuslich et al. |
| 5,490,750 A | 2/1996 | Gundy |
| 5,499,892 A | 3/1996 | Reed |
| 5,501,684 A | 3/1996 | Schlapfer et al. |
| 5,505,731 A | 4/1996 | Tornier |
| 5,507,745 A | 4/1996 | Logroscino et al. |
| 5,507,747 A | 4/1996 | Yuan et al. |
| 5,534,001 A | 7/1996 | Schlapfer et al. |
| 5,540,688 A | 7/1996 | Navas |
| 5,545,165 A | 8/1996 | Biedermann et al. |
| 5,549,607 A | 8/1996 | Olson et al. |
| 5,549,608 A | 8/1996 | Errico et al. |
| 5,554,157 A | 9/1996 | Errico et al. |
| 5,562,660 A | 10/1996 | Grob |
| 5,562,663 A | 10/1996 | Wisnewski et al. |
| 5,569,247 A | 10/1996 | Morrison |
| 5,569,251 A | 10/1996 | Baker et al. |
| 5,578,033 A | 11/1996 | Errico et al. |
| 5,584,834 A | 12/1996 | Errico et al. |
| 5,586,984 A | 12/1996 | Errico et al. |
| 5,591,166 A | 1/1997 | Bernhardt et al. |
| 5,601,553 A | 2/1997 | Trebing et al. |
| 5,605,458 A | 2/1997 | Bailey et al. |
| 5,607,304 A | 3/1997 | Bailey et al. |

(56) References Cited

U.S. PATENT DOCUMENTS

| | | |
|---|---|---|
| 5,607,425 A | 3/1997 | Rogozinski |
| 5,607,426 A | 3/1997 | Ralph et al. |
| 5,607,428 A | 3/1997 | Lin |
| 5,609,593 A | 3/1997 | Errico et al. |
| 5,609,594 A | 3/1997 | Errico et al. |
| 5,611,800 A | 3/1997 | Davis et al. |
| 5,628,740 A | 5/1997 | Mullane |
| 5,630,817 A | 5/1997 | Rokegem |
| 5,641,256 A | 6/1997 | Gundy |
| 5,643,260 A | 7/1997 | Doherty |
| 5,643,261 A | 7/1997 | Schafer et al. |
| 5,647,873 A | 7/1997 | Errico et al. |
| 5,653,710 A | 8/1997 | Harle |
| 5,662,652 A | 9/1997 | Schafer et al. |
| 5,662,653 A | 9/1997 | Songer et al. |
| 5,667,508 A | 9/1997 | Errico et al. |
| 5,669,909 A | 9/1997 | Zdeblick et al. |
| 5,669,911 A | 9/1997 | Errico et al. |
| 5,672,175 A | 9/1997 | Martin |
| 5,672,176 A | 9/1997 | Biedermann |
| 5,676,665 A | 10/1997 | Bryan |
| 5,676,703 A | 10/1997 | Gelbard |
| 5,681,319 A | 10/1997 | Biedermann et al. |
| 5,683,390 A | 11/1997 | Metz-Stavenhagen et al. |
| 5,683,391 A | 11/1997 | Boyd |
| 5,690,630 A | 11/1997 | Errico et al. |
| 5,702,393 A | 12/1997 | Pfaifer |
| 5,711,709 A | 1/1998 | McCoy |
| 5,713,705 A | 2/1998 | Grunbichler |
| 5,713,898 A | 2/1998 | Stuecker et al. |
| 5,716,356 A | 2/1998 | Biedermann et al. |
| 5,720,751 A | 2/1998 | Jackson |
| 5,723,013 A | 3/1998 | Jeanson et al. |
| 5,725,527 A | 3/1998 | Biedermann et al. |
| 5,725,528 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,741,254 A | 4/1998 | Henry et al. |
| 5,752,957 A | 5/1998 | Ralph et al. |
| 5,782,833 A | 7/1998 | Haider |
| 5,797,911 A | 8/1998 | Sherman et al. |
| 5,800,435 A | 9/1998 | Errico et al. |
| 5,800,547 A | 9/1998 | Schafer et al. |
| 5,817,094 A | 10/1998 | Errico et al. |
| 5,863,293 A | 1/1999 | Richelsoph |
| 5,873,878 A | 2/1999 | Harms et al. |
| D407,302 S | 3/1999 | Lawson |
| 5,876,402 A | 3/1999 | Errico et al. |
| 5,879,351 A | 3/1999 | Viart |
| 5,882,350 A | 3/1999 | Ralph et al. |
| 5,902,303 A | 5/1999 | Eckhof et al. |
| RE36,221 E | 6/1999 | Breard et al. |
| 5,910,141 A | 6/1999 | Morrison et al. |
| 5,910,142 A | 6/1999 | Tatar |
| 5,928,236 A | 7/1999 | Augagneur et al. |
| 5,938,663 A | 8/1999 | Petreto |
| 5,941,880 A | 8/1999 | Errico et al. |
| 5,944,465 A | 8/1999 | Janitzki |
| 5,951,553 A | 9/1999 | Betz et al. |
| 5,961,517 A | 10/1999 | Biedermann et al. |
| 5,964,760 A | 10/1999 | Richelsoph |
| 5,964,767 A | 10/1999 | Tapia et al. |
| 5,997,539 A | 12/1999 | Errico et al. |
| 6,001,098 A | 12/1999 | Metz-Stavenhagen et al. |
| 6,004,349 A | 12/1999 | Jackson |
| 6,006,930 A | 12/1999 | Dreyer et al. |
| 6,010,503 A | 1/2000 | Richelsoph et al. |
| 6,019,759 A | 2/2000 | Rogozinski |
| 6,022,350 A | 2/2000 | Ganem |
| 6,053,078 A | 4/2000 | Parker |
| 6,056,753 A | 5/2000 | Jackson |
| 6,063,088 A | 5/2000 | Winslow |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,110,172 A | 8/2000 | Jackson |
| 6,113,601 A | 9/2000 | Tatar |
| 6,117,137 A | 9/2000 | Halm et al. |
| 6,129,763 A | 10/2000 | Chauvin et al. |
| 6,132,431 A | 10/2000 | Nilsson et al. |
| 6,136,002 A | 10/2000 | Shih et al. |
| 6,136,003 A | 10/2000 | Hoeck et al. |
| 6,139,549 A | 10/2000 | Keller |
| 6,143,032 A | 11/2000 | Schaefer et al. |
| 6,146,383 A | 11/2000 | Studer et al. |
| 6,149,533 A | 11/2000 | Finn |
| 6,162,223 A | 12/2000 | Orsak et al. |
| 6,168,597 B1 | 1/2001 | Biedermann et al. |
| 6,183,472 B1 | 2/2001 | Lutz |
| 6,186,718 B1 | 2/2001 | Fogard |
| 6,193,719 B1 | 2/2001 | Gournay et al. |
| 6,193,720 B1 | 2/2001 | Yuan et al. |
| 6,214,012 B1 | 4/2001 | Karpman et al. |
| RE37,161 E | 5/2001 | Michelson et al. |
| 6,224,596 B1 | 5/2001 | Jackson |
| 6,224,598 B1 | 5/2001 | Jackson |
| 6,235,028 B1 | 5/2001 | Brumfield et al. |
| 6,235,034 B1 | 5/2001 | Bray |
| 6,241,730 B1 | 6/2001 | Alby |
| 6,241,731 B1 | 6/2001 | Fiz |
| 6,248,105 B1 | 6/2001 | Schlapfer et al. |
| 6,248,107 B1 | 6/2001 | Foley et al. |
| 6,251,112 B1 | 6/2001 | Jackson |
| 6,254,146 B1 | 7/2001 | Church |
| 6,254,602 B1 | 7/2001 | Justis |
| 6,261,039 B1 | 7/2001 | Reed |
| 6,267,764 B1 | 7/2001 | Elberg |
| 6,267,765 B1 | 7/2001 | Taylor et al. |
| 6,280,445 B1 | 8/2001 | Morrison et al. |
| 6,287,308 B1 | 9/2001 | Betz et al. |
| 6,296,642 B1 | 10/2001 | Morrison et al. |
| 6,296,643 B1 | 10/2001 | Hopf et al. |
| 6,299,613 B1 | 10/2001 | Ogilvie et al. |
| 6,299,616 B1 | 10/2001 | Beger |
| 6,302,888 B1 | 10/2001 | Mellinger et al. |
| 6,309,391 B1 | 10/2001 | Crandall et al. |
| 6,315,564 B1 | 11/2001 | Levisman |
| 6,322,108 B1 | 11/2001 | Riesselmann et al. |
| RE37,665 E | 4/2002 | Ralph et al. |
| 6,368,321 B1 | 4/2002 | Jackson |
| 6,371,957 B1 | 4/2002 | Amrein |
| 6,379,356 B1 | 4/2002 | Jackson |
| 6,402,757 B1 | 6/2002 | Moore et al. |
| 6,412,831 B1 | 7/2002 | Noel et al. |
| 6,440,133 B1 | 8/2002 | Beale et al. |
| 6,443,956 B1 | 9/2002 | Ray |
| 6,467,958 B1 | 10/2002 | Sasaki et al. |
| 6,471,703 B1 | 10/2002 | Ashman |
| 6,478,797 B1 | 11/2002 | Paul |
| 6,478,798 B1 | 11/2002 | Howland |
| 6,485,491 B1 | 11/2002 | Farris et al. |
| 6,485,492 B1 | 11/2002 | Halm et al. |
| 6,485,494 B1 | 11/2002 | Haider |
| 6,520,962 B1 | 2/2003 | Taylor et al. |
| 6,527,804 B1 | 3/2003 | Gauchet et al. |
| 6,533,786 B1 | 3/2003 | Needham et al. |
| 6,554,831 B1 | 4/2003 | Rivard et al. |
| 6,554,834 B1 | 4/2003 | Crozet et al. |
| 6,562,040 B1 | 5/2003 | Wagner |
| 6,565,565 B1 | 5/2003 | Yuan et al. |
| 6,565,567 B1 | 5/2003 | Haider |
| 6,595,992 B1 | 7/2003 | Wagner et al. |
| 6,602,255 B1 | 8/2003 | Campbell et al. |
| 6,613,050 B1 | 9/2003 | Wagner et al. |
| 6,616,667 B1 | 9/2003 | Steiger et al. |
| 6,648,885 B1 | 11/2003 | Friesem |
| 6,648,888 B1 | 11/2003 | Shluzas |
| 6,652,526 B1 | 11/2003 | Arafiles |
| 6,652,765 B1 | 11/2003 | Beaty |

(56) References Cited

U.S. PATENT DOCUMENTS

| | | |
|---|---|---|
| 6,656,179 B1 | 12/2003 | Schaefer et al. |
| 6,663,632 B1 | 12/2003 | Frigg |
| 6,673,073 B1 | 1/2004 | Schaefer |
| 6,676,661 B1 | 1/2004 | Benlloch et al. |
| 6,712,818 B1 | 3/2004 | Michelson |
| 6,716,214 B1 | 4/2004 | Jackson |
| 6,743,231 B1 | 6/2004 | Gray et al. |
| 6,755,829 B1 | 6/2004 | Bono et al. |
| 6,778,861 B1 | 8/2004 | Liebrecht et al. |
| 6,835,196 B2 | 12/2004 | Biedermann et al. |
| 6,872,208 B1 | 3/2005 | McBride et al. |
| 6,896,677 B1 | 5/2005 | Lin |
| 6,997,927 B2 | 2/2006 | Jackson |
| 7,001,389 B1 | 2/2006 | Navarro et al. |
| RE39,035 E | 3/2006 | Finn et al. |
| RE39,089 E | 5/2006 | Ralph et al. |
| 7,081,116 B1 | 7/2006 | Carly |
| 7,179,261 B2 | 2/2007 | Sicvol et al. |
| 7,204,838 B2 | 4/2007 | Jackson |
| 7,316,684 B1 | 1/2008 | Baccelli et al. |
| 7,672,394 B2 | 3/2010 | Duan et al. |
| 7,686,833 B1 | 3/2010 | Muhanna et al. |
| 7,717,942 B2 | 5/2010 | Schumacher |
| 7,766,943 B1 | 8/2010 | Fallin et al. |
| 7,833,251 B1 | 11/2010 | Ahlgren et al. |
| 7,862,587 B2 | 1/2011 | Jackson |
| 7,947,065 B2 | 5/2011 | Hammill, Sr. et al. |
| 7,972,364 B2 | 7/2011 | Biedermann et al. |
| 8,043,340 B1 | 10/2011 | Law |
| 8,092,499 B1 | 1/2012 | Roth |
| 8,114,133 B2 | 2/2012 | Logan |
| 8,114,134 B2 | 2/2012 | Winslow et al. |
| 8,133,262 B2 | 3/2012 | Whipple |
| 8,167,914 B1 | 5/2012 | Hunt et al. |
| 8,197,517 B1 | 6/2012 | Lab et al. |
| 8,206,422 B2 | 6/2012 | Hestad et al. |
| 8,211,110 B1 | 7/2012 | Corin et al. |
| 8,236,035 B1 | 8/2012 | Bedor |
| 8,382,809 B2 | 2/2013 | Kaufman et al. |
| 8,388,659 B1 | 3/2013 | Lab et al. |
| 8,394,133 B2 | 3/2013 | Jackson |
| 8,439,922 B1 | 5/2013 | Arnold et al. |
| 8,439,924 B1 | 5/2013 | McBride et al. |
| 8,444,681 B2 | 5/2013 | Jackson et al. |
| 8,470,009 B1 | 6/2013 | Rezach |
| 8,814,913 B2 | 8/2014 | Jackson |
| 8,911,479 B2 | 12/2014 | Jackson et al. |
| 9,068,587 B2 | 6/2015 | Sage et al. |
| 9,445,847 B2 | 9/2016 | Biedermann et al. |
| 2001/0007941 A1 | 7/2001 | Steiner et al. |
| 2001/0010000 A1 | 7/2001 | Gertzbein et al. |
| 2001/0011172 A1 | 8/2001 | Orbay et al. |
| 2001/0012937 A1 | 8/2001 | Schaffler-Wachter et al. |
| 2001/0023350 A1 | 9/2001 | Choi |
| 2001/0037111 A1 | 11/2001 | Dixon et al. |
| 2001/0041894 A1 | 11/2001 | Campbell et al. |
| 2001/0047173 A1 | 11/2001 | Schlapfer et al. |
| 2001/0047174 A1 | 11/2001 | Donno et al. |
| 2001/0047175 A1 | 11/2001 | Doubler et al. |
| 2001/0052438 A1 | 12/2001 | Spencer |
| 2002/0004683 A1 | 1/2002 | Michelson |
| 2002/0007184 A1 | 1/2002 | Ogilvie et al. |
| 2002/0010467 A1 | 1/2002 | Cooper et al. |
| 2002/0013586 A1 | 1/2002 | Justis et al. |
| 2002/0016594 A1 | 2/2002 | Schlapfer et al. |
| 2002/0022764 A1 | 2/2002 | Smith et al. |
| 2002/0022842 A1 | 2/2002 | Horvath et al. |
| 2002/0029040 A1 | 3/2002 | Morrison et al. |
| 2002/0035365 A1 | 3/2002 | Kumar et al. |
| 2002/0035366 A1 | 3/2002 | Walder et al. |
| 2002/0035367 A1 | 3/2002 | Ritland |
| 2002/0045898 A1 | 4/2002 | Freid et al. |
| 2002/0045899 A1 | 4/2002 | Errico et al. |
| 2002/0049446 A1 | 4/2002 | Harkey, III et al. |
| 2002/0055740 A1 | 5/2002 | Lieberman |
| 2002/0055741 A1 | 5/2002 | Schlapfer et al. |
| 2002/0058942 A1 | 5/2002 | Biedermann et al. |
| 2002/0068975 A1 | 6/2002 | Teitelbaum et al. |
| 2002/0072750 A1 | 6/2002 | Jackson |
| 2002/0072751 A1 | 6/2002 | Jackson |
| 2002/0082602 A1 | 6/2002 | Biedermann et al. |
| 2002/0082603 A1 | 6/2002 | Dixon et al. |
| 2002/0087159 A1 | 7/2002 | Thomas |
| 2002/0087161 A1 | 7/2002 | Randall et al. |
| 2002/0091386 A1 | 7/2002 | Martin et al. |
| 2002/0095153 A1 | 7/2002 | Jones et al. |
| 2002/0095154 A1 | 7/2002 | Atkinson et al. |
| 2002/0095881 A1 | 7/2002 | Shreiner |
| 2002/0103487 A1 | 8/2002 | Errico et al. |
| 2002/0111627 A1 | 8/2002 | Vincent-Prestigiacomo |
| 2002/0116001 A1 | 8/2002 | Schaefer et al. |
| 2002/0120270 A1 | 8/2002 | Trieu et al. |
| 2002/0123752 A1 | 9/2002 | Schultheiss et al. |
| 2002/0133154 A1 | 9/2002 | Saint Martin |
| 2002/0133158 A1 | 9/2002 | Saint Martin |
| 2002/0133159 A1 | 9/2002 | Jackson |
| 2002/0138076 A1 | 9/2002 | Biedermann et al. |
| 2002/0138077 A1 | 9/2002 | Ferree |
| 2002/0143328 A1 | 10/2002 | Shluzas et al. |
| 2002/0143330 A1 | 10/2002 | Shluzas |
| 2002/0143332 A1 | 10/2002 | Lin et al. |
| 2002/0143338 A1 | 10/2002 | Orbay et al. |
| 2002/0143341 A1 | 10/2002 | Biedermann et al. |
| 2002/0161368 A1 | 10/2002 | Foley et al. |
| 2002/0161370 A1 | 10/2002 | Frigg et al. |
| 2002/0173791 A1 | 11/2002 | Howland |
| 2002/0183747 A1 | 12/2002 | Jao et al. |
| 2002/0198526 A1 | 12/2002 | Shaolian et al. |
| 2003/0004519 A1 | 1/2003 | Torode et al. |
| 2003/0023243 A1 | 1/2003 | Biedermann et al. |
| 2003/0028191 A1 | 2/2003 | Shluzas |
| 2003/0032957 A1 | 2/2003 | McKinley |
| 2003/0055426 A1 | 3/2003 | Carbone et al. |
| 2003/0055427 A1 | 3/2003 | Graf |
| 2003/0060826 A1 | 3/2003 | Foley et al. |
| 2003/0073995 A1 | 4/2003 | Reed |
| 2003/0073996 A1 | 4/2003 | Doubler et al. |
| 2003/0073998 A1 | 4/2003 | Pagliuca et al. |
| 2003/0078580 A1 | 4/2003 | Shitoto |
| 2003/0083657 A1 | 5/2003 | Drewry et al. |
| 2003/0083667 A1 | 5/2003 | Ralph et al. |
| 2003/0093077 A1 | 5/2003 | Schlapfer et al. |
| 2003/0093078 A1 | 5/2003 | Ritland |
| 2003/0100896 A1 | 5/2003 | Biedermann et al. |
| 2003/0100897 A1 | 5/2003 | Metz-Stavenhagen |
| 2003/0100904 A1 | 5/2003 | Biedermann |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0120275 A1 | 6/2003 | Lenke et al. |
| 2003/0125741 A1 | 7/2003 | Biedermann et al. |
| 2003/0125749 A1 | 7/2003 | Yuan et al. |
| 2003/0130659 A1 | 7/2003 | Haider |
| 2003/0130661 A1 | 7/2003 | Osman |
| 2003/0135210 A1 | 7/2003 | Dixon et al. |
| 2003/0135217 A1 | 7/2003 | Buttermann et al. |
| 2003/0139745 A1 | 7/2003 | Ashman |
| 2003/0149430 A1 | 8/2003 | Ferrante et al. |
| 2003/0149431 A1 | 8/2003 | Varieur |
| 2003/0149432 A1 | 8/2003 | Frigg et al. |
| 2003/0149435 A1 | 8/2003 | Baynham et al. |
| 2003/0153911 A1 | 8/2003 | Shluzas |
| 2003/0153912 A1 | 8/2003 | Graf |
| 2003/0153920 A1 | 8/2003 | Ralph et al. |
| 2003/0163133 A1 | 8/2003 | Altarac et al. |
| 2003/0167058 A1 | 9/2003 | Shluzas |
| 2003/0171749 A1 | 9/2003 | Le Couedic et al. |
| 2003/0176863 A1 | 9/2003 | Ueyama et al. |
| 2003/0181913 A1 | 9/2003 | Lieberman |
| 2003/0187433 A1 | 10/2003 | Lin |
| 2003/0187434 A1 | 10/2003 | Lin |
| 2003/0191470 A1 | 10/2003 | Ritland |
| 2003/0199872 A1 | 10/2003 | Markworth et al. |
| 2003/0199873 A1 | 10/2003 | Richelsoph |

(56) References Cited

U.S. PATENT DOCUMENTS

| | | |
|---|---|---|
| 2003/0208204 A1 | 11/2003 | Bailey et al. |
| 2003/0212398 A1 | 11/2003 | Jackson |
| 2003/0216735 A1 | 11/2003 | Altarac et al. |
| 2003/0220642 A1 | 11/2003 | Freudiger |
| 2003/0220643 A1 | 11/2003 | Ferree |
| 2003/0225408 A1 | 12/2003 | Nichols et al. |
| 2003/0229345 A1 | 12/2003 | Stahurski |
| 2003/0229347 A1 | 12/2003 | Sherman et al. |
| 2003/0236529 A1 | 12/2003 | Shluzas et al. |
| 2004/0006342 A1 | 1/2004 | Altarac et al. |
| 2004/0039383 A1 | 2/2004 | Jackson |
| 2004/0039384 A1 | 2/2004 | Boehm, Jr. et al. |
| 2004/0039385 A1 | 2/2004 | Mazda et al. |
| 2004/0049189 A1 | 3/2004 | Le Couedic et al. |
| 2004/0049190 A1 | 3/2004 | Biedermann et al. |
| 2004/0049196 A1 | 3/2004 | Jackson |
| 2004/0073215 A1 | 4/2004 | Carli |
| 2004/0073218 A1 | 4/2004 | Dahners |
| 2004/0078051 A1 | 4/2004 | Davison et al. |
| 2004/0078082 A1 | 4/2004 | Lange |
| 2004/0087949 A1 | 5/2004 | Bono et al. |
| 2004/0087950 A1 | 5/2004 | Teitelbaum |
| 2004/0087952 A1 | 5/2004 | Borgstrom et al. |
| 2004/0092934 A1 | 5/2004 | Howland |
| 2004/0092938 A1 | 5/2004 | Carli |
| 2004/0097933 A1 | 5/2004 | Lourdel et al. |
| 2004/0106925 A1 | 6/2004 | Culbert |
| 2004/0111091 A1 | 6/2004 | Ogilvie et al. |
| 2004/0122442 A1 | 6/2004 | Lewis |
| 2004/0127897 A1 | 7/2004 | Freid et al. |
| 2004/0127904 A1 | 7/2004 | Konieczynski et al. |
| 2004/0133207 A1 | 7/2004 | Abdou |
| 2004/0138660 A1 | 7/2004 | Serhan |
| 2004/0138662 A1 | 7/2004 | Landry et al. |
| 2004/0143265 A1 | 7/2004 | Landry et al. |
| 2004/0147928 A1 | 7/2004 | Landry et al. |
| 2004/0147929 A1 | 7/2004 | Biedermann et al. |
| 2004/0147937 A1 | 7/2004 | Dunbar, Jr. et al. |
| 2004/0153068 A1 | 8/2004 | Janowski et al. |
| 2004/0158245 A1 | 8/2004 | Chin |
| 2004/0158247 A1 | 8/2004 | Sitiso et al. |
| 2004/0158258 A1 | 8/2004 | Bonati et al. |
| 2004/0162560 A1 | 8/2004 | Raynor et al. |
| 2004/0167523 A1 | 8/2004 | Jackson |
| 2004/0167524 A1 | 8/2004 | Jackson |
| 2004/0167525 A1 | 8/2004 | Jackson |
| 2004/0172025 A1 | 9/2004 | Drewry et al. |
| 2004/0172031 A1 | 9/2004 | Rubecamp et al. |
| 2004/0172032 A1 | 9/2004 | Jackson |
| 2004/0176776 A1 | 9/2004 | Zubok et al. |
| 2004/0186473 A1 | 9/2004 | Cournoyer et al. |
| 2004/0186474 A1 | 9/2004 | Matthis et al. |
| 2004/0186475 A1 | 9/2004 | Falahee |
| 2004/0210216 A1 | 10/2004 | Farris et al. |
| 2004/0210227 A1 | 10/2004 | Trail et al. |
| 2004/0215190 A1 | 10/2004 | Nguyen et al. |
| 2004/0215191 A1 | 10/2004 | Kitchen |
| 2004/0220567 A1 | 11/2004 | Eisermann et al. |
| 2004/0220671 A1 | 11/2004 | Ralph et al. |
| 2004/0225289 A1 | 11/2004 | Biedermann et al. |
| 2004/0230100 A1 | 11/2004 | Shluzas |
| 2004/0236327 A1 | 11/2004 | Paul et al. |
| 2004/0236328 A1 | 11/2004 | Paul et al. |
| 2004/0236330 A1 | 11/2004 | Purcell et al. |
| 2004/0249378 A1 | 12/2004 | Saint Martin et al. |
| 2004/0254574 A1 | 12/2004 | Morrison et al. |
| 2004/0260283 A1 | 12/2004 | Wu et al. |
| 2004/0267264 A1 | 12/2004 | Konieczynski et al. |
| 2005/0010219 A1 | 1/2005 | Dalton |
| 2005/0021036 A1 | 1/2005 | Whitmore et al. |
| 2005/0027296 A1 | 2/2005 | Thramann et al. |
| 2005/0033298 A1 | 2/2005 | Hawkes et al. |
| 2005/0033436 A1 | 2/2005 | Schlapfer et al. |
| 2005/0033439 A1 | 2/2005 | Gordon et al. |
| 2005/0038430 A1 | 2/2005 | McKinley |
| 2005/0038432 A1 | 2/2005 | Shaolian et al. |
| 2005/0038433 A1 | 2/2005 | Young |
| 2005/0049588 A1 | 3/2005 | Jackson |
| 2005/0049589 A1 | 3/2005 | Jackson |
| 2005/0055026 A1 | 3/2005 | Biedermann et al. |
| 2005/0065514 A1 | 3/2005 | Studer |
| 2005/0065515 A1 | 3/2005 | Jahng |
| 2005/0065516 A1 | 3/2005 | Jahng |
| 2005/0065517 A1 | 3/2005 | Chin |
| 2005/0070899 A1 | 3/2005 | Doubler et al. |
| 2005/0070901 A1 | 3/2005 | David |
| 2005/0080415 A1 | 4/2005 | Keyer et al. |
| 2005/0085812 A1 | 4/2005 | Sherman et al. |
| 2005/0085813 A1 | 4/2005 | Spitler et al. |
| 2005/0085815 A1 | 4/2005 | Harms et al. |
| 2005/0085816 A1 | 4/2005 | Michelson |
| 2005/0090821 A1 | 4/2005 | Berrevoets et al. |
| 2005/0096652 A1 | 5/2005 | Burton |
| 2005/0096653 A1 | 5/2005 | Doubler et al. |
| 2005/0096654 A1 | 5/2005 | Lin |
| 2005/0107788 A1 | 5/2005 | Beaurain et al. |
| 2005/0113927 A1 | 5/2005 | Malek |
| 2005/0119658 A1 | 6/2005 | Ralph et al. |
| 2005/0124991 A1 | 6/2005 | Jahng |
| 2005/0131404 A1 | 6/2005 | Mazda et al. |
| 2005/0131405 A1 | 6/2005 | Molz, IV et al. |
| 2005/0131406 A1 | 6/2005 | Reiley et al. |
| 2005/0131407 A1 | 6/2005 | Sicvol et al. |
| 2005/0131408 A1 | 6/2005 | Sicvol et al. |
| 2005/0131413 A1 | 6/2005 | O'Driscoll et al. |
| 2005/0131419 A1 | 6/2005 | McCord et al. |
| 2005/0131421 A1 | 6/2005 | Anderson et al. |
| 2005/0131422 A1 | 6/2005 | Anderson |
| 2005/0137594 A1 | 6/2005 | Doubler et al. |
| 2005/0137597 A1 | 6/2005 | Butler et al. |
| 2005/0141986 A1 | 6/2005 | Flesher |
| 2005/0143737 A1 | 6/2005 | Pafford et al. |
| 2005/0143823 A1 | 6/2005 | Boyd et al. |
| 2005/0149020 A1 | 7/2005 | Jahng |
| 2005/0149053 A1 | 7/2005 | Varieur |
| 2005/0154389 A1 | 7/2005 | Selover et al. |
| 2005/0154390 A1 | 7/2005 | Biedermann et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0171543 A1 | 8/2005 | Timm et al. |
| 2005/0177154 A1 | 8/2005 | Moumene et al. |
| 2005/0177166 A1 | 8/2005 | Timm et al. |
| 2005/0182401 A1 | 8/2005 | Timm et al. |
| 2005/0182410 A1 | 8/2005 | Jackson |
| 2005/0187548 A1 | 8/2005 | Butler et al. |
| 2005/0187555 A1 | 8/2005 | Biedermann et al. |
| 2005/0192571 A1 | 9/2005 | Abdelgany |
| 2005/0192572 A1 | 9/2005 | Abdelgany et al. |
| 2005/0192573 A1 | 9/2005 | Abdelgany et al. |
| 2005/0192579 A1 | 9/2005 | Jackson |
| 2005/0192580 A1 | 9/2005 | Dalton |
| 2005/0192589 A1 | 9/2005 | Raymond et al. |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203516 A1 | 9/2005 | Biedermann et al. |
| 2005/0203518 A1 | 9/2005 | Biedermann et al. |
| 2005/0203519 A1 | 9/2005 | Harms et al. |
| 2005/0215999 A1 | 9/2005 | Birkmeyer et al. |
| 2005/0216000 A1 | 9/2005 | Colleran et al. |
| 2005/0216001 A1 | 9/2005 | David |
| 2005/0216003 A1 | 9/2005 | Biedermann et al. |
| 2005/0228326 A1 | 10/2005 | Kalfas et al. |
| 2005/0228379 A1 | 10/2005 | Jackson |
| 2005/0228385 A1 | 10/2005 | Lee et al. |
| 2005/0228400 A1 | 10/2005 | Chao |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0234453 A1 | 10/2005 | Shaolian et al. |
| 2005/0234454 A1 | 10/2005 | Chin |

(56) References Cited

U.S. PATENT DOCUMENTS

| | | |
|---|---|---|
| 2005/0234456 A1 | 10/2005 | Malandain |
| 2005/0234459 A1 | 10/2005 | Falahee et al. |
| 2005/0240181 A1 | 10/2005 | Boomer et al. |
| 2005/0240183 A1 | 10/2005 | Vaughan |
| 2005/0245930 A1 | 11/2005 | Timm et al. |
| 2005/0251137 A1 | 11/2005 | Ball |
| 2005/0251139 A1 | 11/2005 | Roh |
| 2005/0251140 A1 | 11/2005 | Shaolian et al. |
| 2005/0251141 A1 | 11/2005 | Frigg et al. |
| 2005/0260058 A1 | 11/2005 | Cassagne, III |
| 2005/0261687 A1 | 11/2005 | Garamszegi et al. |
| 2005/0267470 A1 | 12/2005 | McBride |
| 2005/0267471 A1 | 12/2005 | Biedermann et al. |
| 2005/0267472 A1 | 12/2005 | Biedermann et al. |
| 2005/0267474 A1 | 12/2005 | Dalton |
| 2005/0267477 A1 | 12/2005 | Jackson |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277922 A1 | 12/2005 | Trieu et al. |
| 2005/0277923 A1 | 12/2005 | Sweeney |
| 2005/0277925 A1 | 12/2005 | Mujwid |
| 2005/0277927 A1 | 12/2005 | Guenther et al. |
| 2005/0277928 A1 | 12/2005 | Boschert |
| 2005/0277931 A1 | 12/2005 | Sweeney et al. |
| 2005/0277934 A1 | 12/2005 | Vardiman |
| 2005/0278023 A1 | 12/2005 | Zwirkoski |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0283244 A1 | 12/2005 | Gordon et al. |
| 2005/0288669 A1 | 12/2005 | Abdou |
| 2005/0288670 A1 | 12/2005 | Panjabi |
| 2005/0288672 A1 | 12/2005 | Ferree |
| 2005/0288673 A1 | 12/2005 | Catbagan et al. |
| 2006/0004359 A1 | 1/2006 | Kramer et al. |
| 2006/0004363 A1 | 1/2006 | Brockmeyer et al. |
| 2006/0009767 A1 | 1/2006 | Kiester |
| 2006/0009769 A1 | 1/2006 | Lieberman |
| 2006/0009770 A1 | 1/2006 | Speirs et al. |
| 2006/0009773 A1 | 1/2006 | Jackson |
| 2006/0009780 A1 | 1/2006 | Foley et al. |
| 2006/0015099 A1 | 1/2006 | Cannon et al. |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0025771 A1 | 2/2006 | Jackson |
| 2006/0030850 A1 | 2/2006 | Keegan et al. |
| 2006/0036240 A1 | 2/2006 | Colleran et al. |
| 2006/0036242 A1 | 2/2006 | Nilsson et al. |
| 2006/0036243 A1 | 2/2006 | Sasso et al. |
| 2006/0036244 A1 | 2/2006 | Spitler et al. |
| 2006/0036246 A1 | 2/2006 | Carl et al. |
| 2006/0036252 A1 | 2/2006 | Baynham et al. |
| 2006/0036254 A1 | 2/2006 | Lim |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0052780 A1 | 3/2006 | Errico et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0058790 A1 | 3/2006 | Carl et al. |
| 2006/0064090 A1 | 3/2006 | Park |
| 2006/0064091 A1 | 3/2006 | Ludwig et al. |
| 2006/0064092 A1 | 3/2006 | Howland |
| 2006/0069390 A1 | 3/2006 | Frigg et al. |
| 2006/0074418 A1 | 4/2006 | Jackson |
| 2006/0074419 A1 | 4/2006 | Taylor et al. |
| 2006/0079894 A1 | 4/2006 | Colleran et al. |
| 2006/0079895 A1 | 4/2006 | McLeer |
| 2006/0079896 A1 | 4/2006 | Kwak et al. |
| 2006/0079898 A1 | 4/2006 | Ainsworth |
| 2006/0079899 A1 | 4/2006 | Ritland |
| 2006/0083603 A1 | 4/2006 | Jackson |
| 2006/0084977 A1 | 4/2006 | Lieberman |
| 2006/0084980 A1 | 4/2006 | Melkent et al. |
| 2006/0084981 A1 | 4/2006 | Shluzas |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084991 A1 | 4/2006 | Borgstrom et al. |
| 2006/0085069 A1 | 4/2006 | Kim |
| 2006/0085070 A1 | 4/2006 | Kim |
| 2006/0089643 A1 | 4/2006 | Mujwid |
| 2006/0089644 A1 | 4/2006 | Felix |
| 2006/0089645 A1 | 4/2006 | Eckman |
| 2006/0095035 A1 | 5/2006 | Jones et al. |
| 2006/0095037 A1 | 5/2006 | Jones et al. |
| 2006/0095038 A1 | 5/2006 | Jackson |
| 2006/0100621 A1 | 5/2006 | Jackson |
| 2006/0100622 A1 | 5/2006 | Jackson |
| 2006/0106381 A1 | 5/2006 | Ferree et al. |
| 2006/0106394 A1 | 5/2006 | Colleran |
| 2006/0111713 A1 | 5/2006 | Jackson |
| 2006/0111715 A1 | 5/2006 | Jackson |
| 2006/0116677 A1 | 6/2006 | Burd et al. |
| 2006/0122597 A1 | 6/2006 | Jones et al. |
| 2006/0122599 A1 | 6/2006 | Drewry et al. |
| 2006/0129147 A1 | 6/2006 | Biedermann et al. |
| 2006/0129149 A1 | 6/2006 | Iott et al. |
| 2006/0129239 A1 | 6/2006 | Kwak |
| 2006/0142758 A1 | 6/2006 | Petit |
| 2006/0142760 A1 | 6/2006 | McDonnell |
| 2006/0149228 A1 | 7/2006 | Schlapfer et al. |
| 2006/0149229 A1 | 7/2006 | Kwak et al. |
| 2006/0149232 A1 | 7/2006 | Sasing |
| 2006/0149235 A1 | 7/2006 | Jackson |
| 2006/0149238 A1 | 7/2006 | Sherman et al. |
| 2006/0149240 A1 | 7/2006 | Jackson |
| 2006/0149241 A1 | 7/2006 | Richelsoph et al. |
| 2006/0149251 A1 | 7/2006 | Ziolo et al. |
| 2006/0155277 A1 | 7/2006 | Metz-Stavenhagen |
| 2006/0161152 A1 | 7/2006 | Ensign et al. |
| 2006/0166535 A1 | 7/2006 | Brumfield et al. |
| 2006/0167454 A1 | 7/2006 | Ludwig et al. |
| 2006/0167455 A1 | 7/2006 | Clement et al. |
| 2006/0173454 A1 | 8/2006 | Spitler et al. |
| 2006/0173456 A1 | 8/2006 | Hawkes et al. |
| 2006/0184171 A1 | 8/2006 | Biedermann |
| 2006/0184180 A1 | 8/2006 | Augostino |
| 2006/0189983 A1 | 8/2006 | Fallin et al. |
| 2006/0189985 A1 | 8/2006 | Lewis |
| 2006/0195090 A1 | 8/2006 | Suddaby |
| 2006/0195093 A1 | 8/2006 | Jahng |
| 2006/0195198 A1 | 8/2006 | James |
| 2006/0200128 A1 | 9/2006 | Mueller |
| 2006/0200130 A1 | 9/2006 | Hawkins et al. |
| 2006/0200131 A1 | 9/2006 | Chao et al. |
| 2006/0200132 A1 | 9/2006 | Chao et al. |
| 2006/0200133 A1 | 9/2006 | Jackson |
| 2006/0200149 A1 | 9/2006 | Hoy et al. |
| 2006/0241593 A1 | 10/2006 | Sherman et al. |
| 2006/0241595 A1 | 10/2006 | Molz, IV et al. |
| 2006/0241600 A1 | 10/2006 | Ensign et al. |
| 2006/0241601 A1 | 10/2006 | Trautwein et al. |
| 2006/0241603 A1 | 10/2006 | Jackson |
| 2006/0247624 A1 | 11/2006 | Banouskou et al. |
| 2006/0247630 A1 | 11/2006 | Iott et al. |
| 2006/0247631 A1 | 11/2006 | Ahn et al. |
| 2006/0247632 A1 | 11/2006 | Winslow et al. |
| 2006/0247633 A1 | 11/2006 | Winslow et al. |
| 2006/0247635 A1 | 11/2006 | Gordon et al. |
| 2006/0247658 A1 | 11/2006 | Pond, Jr. et al. |
| 2006/0247779 A1 | 11/2006 | Gordon |
| 2006/0260483 A1 | 11/2006 | Hartmann et al. |
| 2006/0264933 A1 | 11/2006 | Baker et al. |
| 2006/0264934 A1 | 11/2006 | Fallin |
| 2006/0264935 A1 | 11/2006 | White |

(56) References Cited

U.S. PATENT DOCUMENTS

| | | |
|---|---|---|
| 2006/0264936 A1 | 11/2006 | Partin et al. |
| 2006/0264962 A1 | 11/2006 | Chin et al. |
| 2006/0276787 A1 | 12/2006 | Zubok et al. |
| 2006/0276789 A1 | 12/2006 | Jackson |
| 2006/0276791 A1 | 12/2006 | Shluzas |
| 2006/0276792 A1 | 12/2006 | Ensign et al. |
| 2006/0282075 A1 | 12/2006 | Labrom et al. |
| 2006/0282076 A1 | 12/2006 | Labrom et al. |
| 2006/0282077 A1 | 12/2006 | Labrom et al. |
| 2006/0282078 A1 | 12/2006 | Labrom et al. |
| 2006/0282079 A1 | 12/2006 | Labrom et al. |
| 2006/0282080 A1 | 12/2006 | Albert |
| 2006/0293657 A1 | 12/2006 | Hartmann |
| 2006/0293659 A1 | 12/2006 | Alvarez |
| 2006/0293663 A1 | 12/2006 | Walkenhorst |
| 2006/0293666 A1 | 12/2006 | Matthis et al. |
| 2006/0293693 A1 | 12/2006 | Farr et al. |
| 2007/0005062 A1 | 1/2007 | Lange et al. |
| 2007/0005063 A1 | 1/2007 | Bruneau et al. |
| 2007/0005137 A1 | 1/2007 | Kwak |
| 2007/0016190 A1 | 1/2007 | Martinez et al. |
| 2007/0016194 A1 | 1/2007 | Shaolian et al. |
| 2007/0016200 A1 | 1/2007 | Jackson |
| 2007/0021750 A1 | 1/2007 | Shluzas et al. |
| 2007/0032123 A1 | 2/2007 | Timm et al. |
| 2007/0043356 A1 | 2/2007 | Timm et al. |
| 2007/0043357 A1 | 2/2007 | Kirschman |
| 2007/0043358 A1 | 2/2007 | Molz, IV et al. |
| 2007/0043359 A1 | 2/2007 | Altarac et al. |
| 2007/0043364 A1 | 2/2007 | Cawley et al. |
| 2007/0049931 A1 | 3/2007 | Justis et al. |
| 2007/0049933 A1 | 3/2007 | Ahn et al. |
| 2007/0049936 A1 | 3/2007 | Colleran et al. |
| 2007/0055236 A1 | 3/2007 | Hudgins et al. |
| 2007/0055239 A1 | 3/2007 | Sweeney et al. |
| 2007/0055240 A1 | 3/2007 | Matthis et al. |
| 2007/0055241 A1 | 3/2007 | Matthis et al. |
| 2007/0055242 A1 | 3/2007 | Bailly |
| 2007/0055244 A1 | 3/2007 | Jackson |
| 2007/0073289 A1 | 3/2007 | Kwak et al. |
| 2007/0073290 A1 | 3/2007 | Boehm, Jr. |
| 2007/0073291 A1 | 3/2007 | Cordaro et al. |
| 2007/0073293 A1 | 3/2007 | Martz et al. |
| 2007/0073294 A1 | 3/2007 | Chin et al. |
| 2007/0078460 A1 | 4/2007 | Frigg et al. |
| 2007/0078461 A1 | 4/2007 | Shluzas |
| 2007/0083199 A1 | 4/2007 | Baccelli |
| 2007/0088357 A1 | 4/2007 | Johnson et al. |
| 2007/0088359 A1 | 4/2007 | Woods et al. |
| 2007/0090238 A1 | 4/2007 | Justis |
| 2007/0093813 A1 | 4/2007 | Callahan et al. |
| 2007/0093814 A1 | 4/2007 | Callahan, II et al. |
| 2007/0093815 A1 | 4/2007 | Callahan, II et al. |
| 2007/0093818 A1 | 4/2007 | Biedermann et al. |
| 2007/0093819 A1 | 4/2007 | Albert |
| 2007/0093824 A1 | 4/2007 | Hestad et al. |
| 2007/0093826 A1 | 4/2007 | Hawkes et al. |
| 2007/0093833 A1 | 4/2007 | Kuiper et al. |
| 2007/0100341 A1 | 5/2007 | Reglos et al. |
| 2007/0118117 A1 | 5/2007 | Altarac et al. |
| 2007/0118118 A1 | 5/2007 | Kwak et al. |
| 2007/0118119 A1 | 5/2007 | Hestad |
| 2007/0118122 A1 | 5/2007 | Butler et al. |
| 2007/0118123 A1 | 5/2007 | Strausbaugh et al. |
| 2007/0118124 A1 | 5/2007 | Biedermann et al. |
| 2007/0123867 A1 | 5/2007 | Kirschman |
| 2007/0123870 A1 | 5/2007 | Jeon et al. |
| 2007/0129729 A1 | 6/2007 | Petit et al. |
| 2007/0156142 A1 | 7/2007 | Rezach et al. |
| 2007/0161986 A1 | 7/2007 | Levy |
| 2007/0161991 A1 | 7/2007 | Altarac et al. |
| 2007/0161994 A1 | 7/2007 | Lowery et al. |
| 2007/0161995 A1 | 7/2007 | Trautwein et al. |
| 2007/0161996 A1 | 7/2007 | Biedermann et al. |
| 2007/0161997 A1 | 7/2007 | Thramann et al. |
| 2007/0161999 A1 | 7/2007 | Biedermann et al. |
| 2007/0167948 A1 | 7/2007 | Abdou |
| 2007/0167949 A1 | 7/2007 | Altarac et al. |
| 2007/0173818 A1 | 7/2007 | Hestad et al. |
| 2007/0173819 A1 | 7/2007 | Sandlin |
| 2007/0173820 A1 | 7/2007 | Trieu |
| 2007/0173822 A1 | 7/2007 | Bruneau et al. |
| 2007/0173828 A1 | 7/2007 | Firkins et al. |
| 2007/0173832 A1 | 7/2007 | Tebbe et al. |
| 2007/0191832 A1 | 8/2007 | Trieu |
| 2007/0191839 A1 | 8/2007 | Justis et al. |
| 2007/0191841 A1 | 8/2007 | Justis et al. |
| 2007/0191846 A1 | 8/2007 | Bruneau et al. |
| 2007/0198014 A1 | 8/2007 | Graf et al. |
| 2007/0208344 A1 | 9/2007 | Young |
| 2007/0213720 A1 | 9/2007 | Gordon et al. |
| 2007/0219554 A1 | 9/2007 | Landry et al. |
| 2007/0225707 A1 | 9/2007 | Wisnewski et al. |
| 2007/0225708 A1 | 9/2007 | Biedermann et al. |
| 2007/0225711 A1 | 9/2007 | Ensign |
| 2007/0233073 A1 | 10/2007 | Wisnewski et al. |
| 2007/0233078 A1 | 10/2007 | Justis et al. |
| 2007/0233080 A1 | 10/2007 | Na et al. |
| 2007/0233085 A1 | 10/2007 | Biedermann et al. |
| 2007/0233086 A1 | 10/2007 | Harms et al. |
| 2007/0233089 A1 | 10/2007 | Dipoto et al. |
| 2007/0233092 A1 | 10/2007 | Falahee |
| 2007/0233094 A1 | 10/2007 | Colleran et al. |
| 2007/0233095 A1 | 10/2007 | Schlapfer |
| 2007/0233155 A1 | 10/2007 | Lovell |
| 2007/0244481 A1 | 10/2007 | Timm |
| 2007/0244482 A1 | 10/2007 | Aferzon |
| 2007/0250061 A1 | 10/2007 | Chin et al. |
| 2007/0260243 A1 | 11/2007 | Kagami |
| 2007/0270813 A1 | 11/2007 | Garamszegi |
| 2007/0270821 A1 | 11/2007 | Trieu et al. |
| 2007/0270836 A1 | 11/2007 | Bruneau et al. |
| 2007/0270837 A1 | 11/2007 | Eckhardt et al. |
| 2007/0270838 A1 | 11/2007 | Bruneau et al. |
| 2007/0270843 A1 | 11/2007 | Matthis et al. |
| 2007/0270869 A1 | 11/2007 | Young et al. |
| 2007/0276371 A1 | 11/2007 | Baynham et al. |
| 2007/0276379 A1 | 11/2007 | Miller et al. |
| 2007/0276380 A1 | 11/2007 | Jahng et al. |
| 2007/0288004 A1 | 12/2007 | Alvarez |
| 2007/0288012 A1 | 12/2007 | Colleran et al. |
| 2007/0293862 A1 | 12/2007 | Jackson |
| 2008/0009862 A1 | 1/2008 | Hoffman |
| 2008/0009864 A1 | 1/2008 | Forton et al. |
| 2008/0015578 A1 | 1/2008 | Erickson et al. |
| 2008/0015579 A1 | 1/2008 | Whipple |
| 2008/0015580 A1 | 1/2008 | Chao |
| 2008/0015597 A1 | 1/2008 | Whipple |
| 2008/0021454 A1 | 1/2008 | Chao et al. |
| 2008/0021455 A1 | 1/2008 | Chao et al. |
| 2008/0021462 A1 | 1/2008 | Trieu |
| 2008/0021464 A1 | 1/2008 | Morin et al. |
| 2008/0021465 A1 | 1/2008 | Shadduck et al. |
| 2008/0027432 A1 | 1/2008 | Strauss et al. |
| 2008/0039843 A1 | 2/2008 | Abdou |
| 2008/0045951 A1 | 2/2008 | Fanger et al. |
| 2008/0045955 A1 | 2/2008 | Berrevoets et al. |
| 2008/0051780 A1 | 2/2008 | Vaidya et al. |
| 2008/0051787 A1 | 2/2008 | Remington et al. |
| 2008/0058811 A1 | 3/2008 | Alleyne et al. |
| 2008/0058812 A1 | 3/2008 | Zehnder |
| 2008/0065071 A1 | 3/2008 | Park |
| 2008/0065073 A1 | 3/2008 | Perriello et al. |
| 2008/0065075 A1 | 3/2008 | Dant |
| 2008/0065077 A1 | 3/2008 | Ferree |
| 2008/0065079 A1 | 3/2008 | Bruneau et al. |
| 2008/0071273 A1 | 3/2008 | Hawkes et al. |
| 2008/0071274 A1 | 3/2008 | Ensign |
| 2008/0077136 A1 | 3/2008 | Triplett et al. |
| 2008/0077138 A1 | 3/2008 | Cohen et al. |
| 2008/0077139 A1 | 3/2008 | Landry et al. |
| 2008/0077143 A1 | 3/2008 | Shluzas |
| 2008/0086131 A1 | 4/2008 | Daly et al. |
| 2008/0086132 A1 | 4/2008 | Biedermann et al. |

(56) References Cited

U.S. PATENT DOCUMENTS

| | | |
|---|---|---|
| 2008/0091213 A1 | 4/2008 | Jackson |
| 2008/0097441 A1 | 4/2008 | Hayes et al. |
| 2008/0103502 A1 | 5/2008 | Capote et al. |
| 2008/0108992 A1 | 5/2008 | Barry et al. |
| 2008/0114362 A1 | 5/2008 | Justis et al. |
| 2008/0114403 A1 | 5/2008 | Kuester et al. |
| 2008/0119849 A1 | 5/2008 | Beardsley et al. |
| 2008/0119857 A1 | 5/2008 | Potash et al. |
| 2008/0119858 A1 | 5/2008 | Potash |
| 2008/0125777 A1 | 5/2008 | Veldman et al. |
| 2008/0125787 A1 | 5/2008 | Doubler et al. |
| 2008/0125813 A1 | 5/2008 | Erickson et al. |
| 2008/0132957 A1 | 6/2008 | Matthis et al. |
| 2008/0140075 A1 | 6/2008 | Ensign et al. |
| 2008/0140076 A1 | 6/2008 | Jackson |
| 2008/0140133 A1 | 6/2008 | Allard et al. |
| 2008/0140136 A1 | 6/2008 | Jackson |
| 2008/0147121 A1 | 6/2008 | Justis et al. |
| 2008/0147122 A1 | 6/2008 | Jackson |
| 2008/0147129 A1 | 6/2008 | Biedermann et al. |
| 2008/0147195 A1 | 6/2008 | Kwak et al. |
| 2008/0154279 A1 | 6/2008 | Schumacher et al. |
| 2008/0154308 A1 | 6/2008 | Sherman et al. |
| 2008/0154315 A1 | 6/2008 | Jackson |
| 2008/0161857 A1 | 7/2008 | Hestad et al. |
| 2008/0161863 A1 | 7/2008 | Arnold et al. |
| 2008/0167687 A1 | 7/2008 | Colleran et al. |
| 2008/0172090 A1 | 7/2008 | Molz |
| 2008/0172091 A1 | 7/2008 | Anderson |
| 2008/0172096 A1 | 7/2008 | Hawkins |
| 2008/0177316 A1 | 7/2008 | Bergeron et al. |
| 2008/0177317 A1 | 7/2008 | Jackson |
| 2008/0177321 A1 | 7/2008 | Drewry et al. |
| 2008/0177322 A1 | 7/2008 | Davis et al. |
| 2008/0177323 A1 | 7/2008 | Null et al. |
| 2008/0177388 A1 | 7/2008 | Patterson et al. |
| 2008/0183212 A1 | 7/2008 | Veldman et al. |
| 2008/0183213 A1 | 7/2008 | Veldman et al. |
| 2008/0183215 A1 | 7/2008 | Altarac et al. |
| 2008/0183216 A1 | 7/2008 | Jackson |
| 2008/0183219 A1 | 7/2008 | Bertram |
| 2008/0183223 A1 | 7/2008 | Jeon et al. |
| 2008/0188898 A1 | 8/2008 | Jackson |
| 2008/0195153 A1 | 8/2008 | Thompson |
| 2008/0195155 A1 | 8/2008 | Hoffman et al. |
| 2008/0195159 A1 | 8/2008 | Kloss et al. |
| 2008/0200918 A1 | 8/2008 | Spitler et al. |
| 2008/0200956 A1 | 8/2008 | Beckwith et al. |
| 2008/0215095 A1 | 9/2008 | Biedermann et al. |
| 2008/0228184 A1 | 9/2008 | Hestad |
| 2008/0228228 A1 | 9/2008 | Hestad et al. |
| 2008/0234736 A1 | 9/2008 | Trieu et al. |
| 2008/0234737 A1 | 9/2008 | Boschert |
| 2008/0234738 A1 | 9/2008 | Zylber et al. |
| 2008/0234739 A1 | 9/2008 | Hudgins et al. |
| 2008/0234744 A1 | 9/2008 | Zylber et al. |
| 2008/0234756 A1 | 9/2008 | Sutcliffe et al. |
| 2008/0234759 A1 | 9/2008 | Marino |
| 2008/0234761 A1 | 9/2008 | Jackson |
| 2008/0243052 A1 | 10/2008 | Pond et al. |
| 2008/0243185 A1 | 10/2008 | Felix et al. |
| 2008/0243193 A1 | 10/2008 | Ensign et al. |
| 2008/0249570 A1 | 10/2008 | Carson et al. |
| 2008/0262548 A1 | 10/2008 | Lange et al. |
| 2008/0262551 A1 | 10/2008 | Rice et al. |
| 2008/0262554 A1 | 10/2008 | Hayes et al. |
| 2008/0262556 A1 | 10/2008 | Jacofsky et al. |
| 2008/0269742 A1 | 10/2008 | Levy et al. |
| 2008/0269804 A1 | 10/2008 | Holt |
| 2008/0269805 A1 | 10/2008 | Dekutoski et al. |
| 2008/0269809 A1 | 10/2008 | Garamszegi |
| 2008/0275456 A1 | 11/2008 | Vonwiller et al. |
| 2008/0275504 A1 | 11/2008 | Bonin et al. |
| 2008/0287994 A1 | 11/2008 | Perez-Cruet et al. |
| 2008/0288002 A1 | 11/2008 | Crall et al. |
| 2008/0294203 A1 | 11/2008 | Kovach et al. |
| 2008/0300630 A1 | 12/2008 | Bonnema et al. |
| 2008/0300631 A1 | 12/2008 | Tornier |
| 2008/0300633 A1 | 12/2008 | Jackson |
| 2008/0306513 A1 | 12/2008 | Winslow et al. |
| 2008/0306525 A1 | 12/2008 | Mitchell et al. |
| 2008/0306526 A1 | 12/2008 | Winslow et al. |
| 2008/0306533 A1 | 12/2008 | Winslow et al. |
| 2008/0306536 A1 | 12/2008 | Frigg et al. |
| 2008/0306540 A1 | 12/2008 | Mitchell et al. |
| 2008/0306543 A1 | 12/2008 | Cain et al. |
| 2008/0312655 A1 | 12/2008 | Kirschman et al. |
| 2008/0312692 A1 | 12/2008 | Brennan et al. |
| 2008/0312696 A1 | 12/2008 | Butters et al. |
| 2008/0312701 A1 | 12/2008 | Butters et al. |
| 2008/0312703 A1 | 12/2008 | Hestad et al. |
| 2008/0312704 A1 | 12/2008 | Hestad et al. |
| 2008/0319482 A1 | 12/2008 | Jackson |
| 2008/0319490 A1 | 12/2008 | Jackson |
| 2009/0005787 A1 | 1/2009 | Crall et al. |
| 2009/0005813 A1 | 1/2009 | Crall et al. |
| 2009/0005814 A1 | 1/2009 | Miller et al. |
| 2009/0012562 A1 | 1/2009 | Hestad et al. |
| 2009/0012567 A1 | 1/2009 | Biedermann et al. |
| 2009/0018557 A1 | 1/2009 | Pisharodi |
| 2009/0018583 A1 | 1/2009 | Song et al. |
| 2009/0024165 A1 | 1/2009 | Ferree |
| 2009/0024169 A1 | 1/2009 | Triplett et al. |
| 2009/0030457 A1 | 1/2009 | Janowski et al. |
| 2009/0030464 A1 | 1/2009 | Hestad et al. |
| 2009/0036929 A1 | 2/2009 | Reglos et al. |
| 2009/0036932 A1 | 2/2009 | Rouyer et al. |
| 2009/0036934 A1 | 2/2009 | Biedermann et al. |
| 2009/0048601 A1 | 2/2009 | Forton et al. |
| 2009/0048631 A1 | 2/2009 | Bhatnagar et al. |
| 2009/0062860 A1 | 3/2009 | Frasier et al. |
| 2009/0062865 A1 | 3/2009 | Schumacher |
| 2009/0062866 A1 | 3/2009 | Jackson |
| 2009/0062867 A1 | 3/2009 | Schumacher |
| 2009/0062914 A1 | 3/2009 | Marino |
| 2009/0069849 A1 | 3/2009 | Oh et al. |
| 2009/0069852 A1 | 3/2009 | Farris et al. |
| 2009/0069853 A1 | 3/2009 | Schumacher |
| 2009/0076550 A1 | 3/2009 | Bernhardt, Jr. et al. |
| 2009/0076552 A1 | 3/2009 | Tornier |
| 2009/0082666 A1 | 3/2009 | Geist et al. |
| 2009/0082812 A1 | 3/2009 | Lewis |
| 2009/0082815 A1 | 3/2009 | Zylber et al. |
| 2009/0082819 A1 | 3/2009 | Blain et al. |
| 2009/0088769 A1 | 4/2009 | Poletti |
| 2009/0088799 A1 | 4/2009 | Yeh |
| 2009/0088803 A1 | 4/2009 | Justis et al. |
| 2009/0088807 A1 | 4/2009 | Castaneda et al. |
| 2009/0093820 A1 | 4/2009 | Trieu et al. |
| 2009/0093843 A1 | 4/2009 | Lemoine et al. |
| 2009/0093846 A1 | 4/2009 | Hestad et al. |
| 2009/0099606 A1 | 4/2009 | Hestad et al. |
| 2009/0099608 A1 | 4/2009 | Szczesny |
| 2009/0105769 A1 | 4/2009 | Rock et al. |
| 2009/0105770 A1 | 4/2009 | Berrevoets et al. |
| 2009/0105771 A1 | 4/2009 | Lei et al. |
| 2009/0105820 A1 | 4/2009 | Jackson |
| 2009/0112265 A1 | 4/2009 | Hudgins et al. |
| 2009/0112266 A1 | 4/2009 | Weng et al. |
| 2009/0112269 A1 | 4/2009 | Lieberman et al. |
| 2009/0118772 A1 | 5/2009 | Diederich et al. |
| 2009/0131983 A1 | 5/2009 | Biedermann et al. |
| 2009/0138044 A1 | 5/2009 | Bergeron et al. |
| 2009/0138052 A1 | 5/2009 | Biedermann et al. |
| 2009/0143827 A1 | 6/2009 | Levy et al. |
| 2009/0143828 A1 | 6/2009 | Stad et al. |
| 2009/0149885 A1 | 6/2009 | Durward et al. |
| 2009/0149892 A1 | 6/2009 | Stad et al. |
| 2009/0157120 A1 | 6/2009 | Marino et al. |
| 2009/0163901 A1 | 6/2009 | Fisher et al. |
| 2009/0163953 A1 | 6/2009 | Biedermann et al. |
| 2009/0163954 A1 | 6/2009 | Kwak |
| 2009/0163955 A1 | 6/2009 | Moumene et al. |
| 2009/0163956 A1 | 6/2009 | Biedermann et al. |

(56) References Cited

U.S. PATENT DOCUMENTS

| | | |
|---|---|---|
| 2009/0163961 A1 | 6/2009 | Kirschman |
| 2009/0163963 A1 | 6/2009 | Berrevoets |
| 2009/0171392 A1 | 7/2009 | Garcia-Bengochea et al. |
| 2009/0171395 A1 | 7/2009 | Jeon et al. |
| 2009/0177232 A1 | 7/2009 | Kiester |
| 2009/0177237 A1 | 7/2009 | Zucherman et al. |
| 2009/0182380 A1 | 7/2009 | Abdelgany |
| 2009/0182430 A1 | 7/2009 | Tyber et al. |
| 2009/0192548 A1 | 7/2009 | Jeon et al. |
| 2009/0192551 A1 | 7/2009 | Cianfrani et al. |
| 2009/0198280 A1 | 8/2009 | Spratt et al. |
| 2009/0198281 A1 | 8/2009 | Rice et al. |
| 2009/0198289 A1 | 8/2009 | Manderson |
| 2009/0198291 A1 | 8/2009 | Kevin et al. |
| 2009/0204155 A1 | 8/2009 | Aschmann |
| 2009/0216278 A1 | 8/2009 | Song |
| 2009/0216280 A1 | 8/2009 | Hutchinson |
| 2009/0221877 A1 | 9/2009 | Woods |
| 2009/0228045 A1 | 9/2009 | Hayes et al. |
| 2009/0240292 A1 | 9/2009 | Butler et al. |
| 2009/0248030 A1 | 10/2009 | Butler et al. |
| 2009/0248075 A1 | 10/2009 | Ogilvie et al. |
| 2009/0248077 A1 | 10/2009 | Johns |
| 2009/0248083 A1 | 10/2009 | Patterson et al. |
| 2009/0248088 A1 | 10/2009 | Biedermann |
| 2009/0254125 A1 | 10/2009 | Predick |
| 2009/0259254 A1 | 10/2009 | Pisharodi |
| 2009/0259257 A1 | 10/2009 | Prevost |
| 2009/0259258 A1 | 10/2009 | Perez-Cruet et al. |
| 2009/0264895 A1 | 10/2009 | Gasperut et al. |
| 2009/0264896 A1 | 10/2009 | Biedermann et al. |
| 2009/0264930 A1 | 10/2009 | McBride |
| 2009/0264933 A1 | 10/2009 | Carls et al. |
| 2009/0270916 A1 | 10/2009 | Ramsay et al. |
| 2009/0270917 A1 | 10/2009 | Boehm |
| 2009/0270920 A1 | 10/2009 | Douget et al. |
| 2009/0270921 A1 | 10/2009 | Krause |
| 2009/0270922 A1 | 10/2009 | Biedermann et al. |
| 2009/0275981 A1 | 11/2009 | Abdelgany et al. |
| 2009/0275983 A1 | 11/2009 | Veldman et al. |
| 2009/0275985 A1 | 11/2009 | Jackson |
| 2009/0275986 A1 | 11/2009 | Prevost et al. |
| 2009/0281542 A1 | 11/2009 | Justis |
| 2009/0281571 A1 | 11/2009 | Weaver et al. |
| 2009/0281572 A1 | 11/2009 | White |
| 2009/0281573 A1 | 11/2009 | Biedermann et al. |
| 2009/0281574 A1 | 11/2009 | Jackson |
| 2009/0287252 A1 | 11/2009 | Marik et al. |
| 2009/0287253 A1 | 11/2009 | Felix et al. |
| 2009/0299411 A1 | 12/2009 | Laskowitz et al. |
| 2009/0299415 A1 | 12/2009 | Pimenta |
| 2009/0306719 A1 | 12/2009 | Meyer, III et al. |
| 2009/0306720 A1 | 12/2009 | Doubler et al. |
| 2009/0312804 A1 | 12/2009 | Gamache et al. |
| 2009/0326582 A1 | 12/2009 | Songer et al. |
| 2009/0326583 A1 | 12/2009 | Moumene et al. |
| 2009/0326586 A1 | 12/2009 | Duarte |
| 2010/0004692 A1 | 1/2010 | Biedermann et al. |
| 2010/0004694 A1 | 1/2010 | Little |
| 2010/0004695 A1 | 1/2010 | Stad et al. |
| 2010/0010540 A1 | 1/2010 | Park |
| 2010/0010542 A1 | 1/2010 | Jackson |
| 2010/0010543 A1 | 1/2010 | Jackson |
| 2010/0023061 A1 | 1/2010 | Randol et al. |
| 2010/0030224 A1 | 2/2010 | Winslow et al. |
| 2010/0030272 A1 | 2/2010 | Winslow et al. |
| 2010/0030283 A1 | 2/2010 | King et al. |
| 2010/0036417 A1 | 2/2010 | James et al. |
| 2010/0036422 A1 | 2/2010 | Flynn et al. |
| 2010/0036423 A1 | 2/2010 | Hayes et al. |
| 2010/0036425 A1 | 2/2010 | Barrus et al. |
| 2010/0036432 A1 | 2/2010 | Ely |
| 2010/0036443 A1 | 2/2010 | Hutton et al. |
| 2010/0042149 A1 | 2/2010 | Chao et al. |
| 2010/0042152 A1 | 2/2010 | Semler et al. |
| 2010/0042155 A1 | 2/2010 | Biedermann et al. |
| 2010/0042156 A1 | 2/2010 | Harms et al. |
| 2010/0057125 A1 | 3/2010 | Viker |
| 2010/0057126 A1 | 3/2010 | Hestad |
| 2010/0057131 A1 | 3/2010 | Ely et al. |
| 2010/0063544 A1 | 3/2010 | Butler |
| 2010/0063545 A1 | 3/2010 | Richelsoph |
| 2010/0063546 A1 | 3/2010 | Miller et al. |
| 2010/0063547 A1 | 3/2010 | Morin et al. |
| 2010/0063550 A1 | 3/2010 | Felix et al. |
| 2010/0063552 A1 | 3/2010 | Chin et al. |
| 2010/0069919 A1 | 3/2010 | Carls et al. |
| 2010/0069969 A1 | 3/2010 | Ampuero et al. |
| 2010/0082066 A1 | 4/2010 | Biyani |
| 2010/0087858 A1 | 4/2010 | Abdou |
| 2010/0087862 A1 | 4/2010 | Biedermann et al. |
| 2010/0087863 A1 | 4/2010 | Biedermann et al. |
| 2010/0087864 A1 | 4/2010 | Klein et al. |
| 2010/0087865 A1 | 4/2010 | Biedermann et al. |
| 2010/0094343 A1 | 4/2010 | Pham et al. |
| 2010/0094348 A1 | 4/2010 | Biedermann et al. |
| 2010/0094349 A1 | 4/2010 | Hammer et al. |
| 2010/0094352 A1 | 4/2010 | Iott et al. |
| 2010/0094353 A1 | 4/2010 | Shim et al. |
| 2010/0100136 A1 | 4/2010 | Won et al. |
| 2010/0100137 A1 | 4/2010 | Justis et al. |
| 2010/0106189 A1 | 4/2010 | Miller |
| 2010/0106192 A1 | 4/2010 | Barry |
| 2010/0114165 A1 | 5/2010 | Ely |
| 2010/0114170 A1 | 5/2010 | Barrus et al. |
| 2010/0114171 A1 | 5/2010 | Boachie-Adjei et al. |
| 2010/0114179 A1 | 5/2010 | Moore et al. |
| 2010/0114180 A1 | 5/2010 | Rock et al. |
| 2010/0114182 A1 | 5/2010 | Wilcox et al. |
| 2010/0121386 A1 | 5/2010 | Peultier et al. |
| 2010/0125302 A1 | 5/2010 | Hammill, Sr. et al. |
| 2010/0137908 A1 | 6/2010 | Zhang |
| 2010/0137912 A1 | 6/2010 | Alcock et al. |
| 2010/0137918 A1 | 6/2010 | Wilcox et al. |
| 2010/0137920 A1 | 6/2010 | Hammill, Sr. et al. |
| 2010/0152776 A1 | 6/2010 | Keyer et al. |
| 2010/0152785 A1 | 6/2010 | Forton et al. |
| 2010/0160965 A1 | 6/2010 | Viker |
| 2010/0160967 A1 | 6/2010 | Capozzoli |
| 2010/0160968 A1 | 6/2010 | Joshi et al. |
| 2010/0160974 A1 | 6/2010 | Viker |
| 2010/0160976 A1 | 6/2010 | Biedermann et al. |
| 2010/0168796 A1 | 7/2010 | Eliasen et al. |
| 2010/0168800 A1 | 7/2010 | Biedermann et al. |
| 2010/0168801 A1 | 7/2010 | Biedermann et al. |
| 2010/0168803 A1 | 7/2010 | Hestad et al. |
| 2010/0174322 A1 | 7/2010 | Abdelgany et al. |
| 2010/0179602 A1 | 7/2010 | Dauster et al. |
| 2010/0191293 A1 | 7/2010 | Jackson |
| 2010/0204735 A1 | 8/2010 | Gephart et al. |
| 2010/0211104 A1 | 8/2010 | Moumene et al. |
| 2010/0211105 A1 | 8/2010 | Moumene et al. |
| 2010/0211114 A1 | 8/2010 | Jackson |
| 2010/0222822 A1 | 9/2010 | Farris et al. |
| 2010/0222828 A1 | 9/2010 | Stad et al. |
| 2010/0228292 A1 | 9/2010 | Arnold et al. |
| 2010/0234902 A1 | 9/2010 | Biedermann et al. |
| 2010/0249843 A1 | 9/2010 | Wegrzyn, III |
| 2010/0249846 A1 | 9/2010 | Simonson |
| 2010/0249856 A1 | 9/2010 | Iott et al. |
| 2010/0262185 A1 | 10/2010 | Gelfand et al. |
| 2010/0262187 A1 | 10/2010 | Marik et al. |
| 2010/0262190 A1 | 10/2010 | Ballard et al. |
| 2010/0262191 A1 | 10/2010 | Marik et al. |
| 2010/0262192 A1 | 10/2010 | Foley |
| 2010/0274285 A1 | 10/2010 | Rouleau |
| 2010/0274287 A1 | 10/2010 | Rouleau et al. |
| 2010/0274288 A1 | 10/2010 | Prevost et al. |
| 2010/0298891 A1 | 11/2010 | Jackson |
| 2010/0305621 A1 | 12/2010 | Wang et al. |
| 2010/0312288 A1 | 12/2010 | Hammill, Sr. et al. |
| 2010/0331885 A1 | 12/2010 | Remington et al. |
| 2011/0004256 A1 | 1/2011 | Biedermann et al. |
| 2011/0009906 A1 | 1/2011 | Hestad et al. |

(56) References Cited

U.S. PATENT DOCUMENTS

| | | | |
|---|---|---|---|
| 2011/0009911 A1 | 1/2011 | Hammill et al. |
| 2011/0029022 A1 | 2/2011 | Zehnder et al. |
| 2011/0040338 A1 | 2/2011 | Jackson |
| 2011/0046683 A1 | 2/2011 | Biedermann et al. |
| 2011/0093015 A1 | 4/2011 | Ramsay et al. |
| 2011/0093021 A1 | 4/2011 | Fanger et al. |
| 2011/0106174 A1 | 5/2011 | Rezach |
| 2011/0106175 A1 | 5/2011 | Rezach |
| 2011/0130792 A1 | 6/2011 | Nydegger et al. |
| 2011/0152939 A1 | 6/2011 | Aldridge |
| 2011/0152949 A1 | 6/2011 | Biedermann et al. |
| 2011/0160778 A1 | 6/2011 | Elsbury |
| 2011/0166610 A1 | 7/2011 | Altarac et al. |
| 2011/0178558 A1 | 7/2011 | Barry |
| 2011/0178560 A1 | 7/2011 | Butler et al. |
| 2011/0184469 A1 | 7/2011 | Ballard et al. |
| 2011/0184471 A1 | 7/2011 | Foley et al. |
| 2011/0190822 A1 | 8/2011 | Spitler et al. |
| 2011/0196430 A1 | 8/2011 | Walsh |
| 2011/0202094 A1 | 8/2011 | Pereira et al. |
| 2011/0202095 A1 | 8/2011 | Semler et al. |
| 2011/0230915 A1 | 9/2011 | Anderson et al. |
| 2011/0238119 A1 | 9/2011 | Moumene et al. |
| 2011/0251644 A1 | 10/2011 | Hestad et al. |
| 2011/0257685 A1 | 10/2011 | Hay et al. |
| 2011/0257687 A1 | 10/2011 | Trieu et al. |
| 2011/0257689 A1 | 10/2011 | Fiechter et al. |
| 2011/0257690 A1 | 10/2011 | Rezach |
| 2011/0263945 A1 | 10/2011 | Peterson et al. |
| 2011/0313460 A1 | 12/2011 | Mclean et al. |
| 2011/0313463 A1 | 12/2011 | McLean |
| 2011/0313471 A1 | 12/2011 | McLean et al. |
| 2012/0029568 A1 | 2/2012 | Jackson |
| 2012/0046699 A1 | 2/2012 | Jones et al. |
| 2012/0053636 A1 | 3/2012 | Schmocker |
| 2012/0071928 A1 | 3/2012 | Jackson |
| 2012/0078307 A1 | 3/2012 | Nihalani |
| 2012/0197314 A1 | 8/2012 | Farris |
| 2012/0232598 A1 | 9/2012 | Hestad et al. |
| 2012/0310284 A1 | 12/2012 | Gerchow |
| 2013/0013003 A1 | 1/2013 | Carbone et al. |
| 2013/0103097 A1 | 4/2013 | May et al. |
| 2013/0150852 A1 | 6/2013 | Shluzas et al. |
| 2014/0012332 A1 | 1/2014 | Jackson |
| 2014/0081334 A1 | 3/2014 | Jackson |
| 2014/0214097 A1 | 7/2014 | Jackson et al. |
| 2015/0094770 A1 | 4/2015 | Jackson et al. |
| 2015/0119942 A1 | 4/2015 | Jackson et al. |
| 2015/0148846 A1 | 5/2015 | Jackson |
| 2015/0164558 A1 | 6/2015 | Jackson et al. |
| 2016/0038188 A1 | 2/2016 | Jackson et al. |
| 2016/0242818 A1 | 8/2016 | Jackson |

FOREIGN PATENT DOCUMENTS

| | | |
|---|---|---|
| DE | 373809 | 4/1923 |
| DE | 3630863 | 3/1988 |
| DE | G9202745.8 | 4/1992 |
| DE | 4425392 | 11/1995 |
| DE | 29810798 | 12/1999 |
| DE | 19951145 | 5/2001 |
| DE | 20207850 U1 | 10/2002 |
| DE | 102007055745 | 7/2008 |
| EP | 0195455 | 9/1986 |
| EP | 0172130 | 2/1987 |
| EP | 0276153 | 7/1988 |
| EP | 0667127 | 8/1995 |
| EP | 0669109 | 8/1995 |
| EP | 0677277 | 10/1995 |
| EP | 1277444 | 1/2003 |
| EP | 2082709 | 7/2009 |
| EP | 2468198 | 12/2010 |
| ES | 2384773 | 7/2012 |
| FR | 2467312 | 4/1981 |
| FR | 2715825 | 8/1995 |
| FR | 2717370 | 9/1995 |
| FR | 2718946 | 10/1995 |
| FR | 2799949 | 4/2001 |
| FR | 2814936 | 4/2002 |
| FR | 2815535 | 4/2002 |
| FR | 2856578 | 6/2003 |
| FR | 2865377 | 1/2004 |
| FR | 2846223 | 4/2004 |
| FR | 2857850 | 4/2004 |
| FR | 2925288 | 6/2009 |
| GB | 203508 | 9/1923 |
| GB | 2082709 | 3/1982 |
| GB | 2140523 | 11/1984 |
| GB | 2365345 | 2/2002 |
| GB | 2382304 | 5/2003 |
| JP | H10277070 | 10/1998 |
| JP | 2000325358 | 3/2000 |
| JP | 2002052030 | 2/2002 |
| JP | 2002221218 | 3/2002 |
| SU | 371359 | 2/1973 |
| WO | 8909030 | 10/1989 |
| WO | 8912431 | 12/1989 |
| WO | 9116018 | 10/1991 |
| WO | 9116020 | 10/1991 |
| WO | 9203100 | 3/1992 |
| WO | 9321848 | 11/1993 |
| WO | 9325161 | 12/1993 |
| WO | 9410927 | 5/1994 |
| WO | 9410944 | 5/1994 |
| WO | 9426191 | 11/1994 |
| WO | 9428824 | 12/1994 |
| WO | 9501132 | 1/1995 |
| WO | 9513755 | 5/1995 |
| WO | WO 95/13755 | 5/1995 |
| WO | 9528889 | 11/1995 |
| WO | 9531947 | 11/1995 |
| WO | 9535067 | 12/1995 |
| WO | 9606576 | 3/1996 |
| WO | 9621396 | 7/1996 |
| WO | 9625104 | 8/1996 |
| WO | 9628105 | 9/1996 |
| WO | 9628118 | 9/1996 |
| WO | 9641582 | 12/1996 |
| WO | 9714366 | 4/1997 |
| WO | 9714368 | 4/1997 |
| WO | 9727812 | 8/1997 |
| WO | 9730649 | 8/1997 |
| WO | 9737604 | 10/1997 |
| WO | 9737605 | 10/1997 |
| WO | 9812977 | 4/1998 |
| WO | 9815233 | 4/1998 |
| WO | 9825534 | 6/1998 |
| WO | 9832386 | 7/1998 |
| WO | 9834554 | 8/1998 |
| WO | 9834556 | 8/1998 |
| WO | 9838924 | 9/1998 |
| WO | 9903415 | 1/1999 |
| WO | 9905980 | 2/1999 |
| WO | 9932084 | 7/1999 |
| WO | 9938463 | 8/1999 |
| WO | 9947083 | 9/1999 |
| WO | 9949802 | 10/1999 |
| WO | 0015125 | 3/2000 |
| WO | 0022997 | 4/2000 |
| WO | 0027297 | 5/2000 |
| WO | 0072769 | 7/2000 |
| WO | 0065268 | 11/2000 |
| WO | 0066045 | 11/2000 |
| WO | 0106940 | 2/2001 |
| WO | 0108574 | 2/2001 |
| WO | 0110317 | 2/2001 |
| WO | 0115612 | 3/2001 |
| WO | 0122893 | 4/2001 |
| WO | 0128435 | 4/2001 |
| WO | 0128436 | 4/2001 |
| WO | 0145576 | 6/2001 |
| WO | 0149191 | 7/2001 |
| WO | 0158370 | 8/2001 |
| WO | 0167972 | 9/2001 |

(56) References Cited

FOREIGN PATENT DOCUMENTS

| | | |
|---|---|---|
| WO | 0167974 | 9/2001 |
| WO | 0222030 | 3/2002 |
| WO | 0234150 | 5/2002 |
| WO | 02054966 | 7/2002 |
| WO | 02102259 | 12/2002 |
| WO | 03007828 | 1/2003 |
| WO | 03026523 | 4/2003 |
| WO | 03037199 | 5/2003 |
| WO | 03047442 | 6/2003 |
| WO | 03068083 | 8/2003 |
| WO | 03068088 | 8/2003 |
| WO | 03084415 | 10/2003 |
| WO | 03094699 | 11/2003 |
| WO | 2004021900 | 3/2004 |
| WO | 2004022108 | 3/2004 |
| WO | 2004041100 | 5/2004 |
| WO | 2004075778 | 9/2004 |
| WO | 2004089245 | 10/2004 |
| WO | 2004098452 | 11/2004 |
| WO | 2004105577 | 12/2004 |
| WO | 2004107997 | 12/2004 |
| WO | 2005000136 | 1/2005 |
| WO | 2005000137 | 1/2005 |
| WO | 2005013839 | 2/2005 |
| WO | 2005018466 | 3/2005 |
| WO | 2005018471 | 3/2005 |
| WO | 2005020829 | 3/2005 |
| WO | 2005030068 | 4/2005 |
| WO | 2005065374 | 7/2005 |
| WO | 2005072632 | 8/2005 |
| WO | 2005082262 | 9/2005 |
| WO | 2005087121 | 9/2005 |
| WO | 2005099400 | 10/2005 |
| WO | 2005102195 | 11/2005 |
| WO | 2005104969 | 11/2005 |
| WO | 2006005198 | 1/2006 |
| WO | 2006017616 | 2/2006 |
| WO | 2006020530 | 2/2006 |
| WO | 2006042188 | 4/2006 |
| WO | 2006047711 | 5/2006 |
| WO | 2006054111 | 5/2006 |
| WO | 2006065607 | 6/2006 |
| WO | 2006066685 | 6/2006 |
| WO | 2006068711 | 6/2006 |
| WO | 2006071742 | 7/2006 |
| WO | 2006079531 | 8/2006 |
| WO | 2006096240 | 9/2006 |
| WO | 2006096351 | 9/2006 |
| WO | 2006200023 | 9/2006 |
| WO | 2006212033 | 9/2006 |
| WO | 2006212034 | 9/2006 |
| WO | 2006217713 | 9/2006 |
| WO | 2006217716 | 9/2006 |
| WO | 2006217719 | 9/2006 |
| WO | 2006104874 | 10/2006 |
| WO | 2006110463 | 10/2006 |
| WO | 2006229608 | 10/2006 |
| WO | 2006229609 | 10/2006 |
| WO | 2006229613 | 10/2006 |
| WO | 2006229614 | 10/2006 |
| WO | 2006229615 | 10/2006 |
| WO | 2006116437 | 11/2006 |
| WO | 2006119447 | 11/2006 |
| WO | 2007002409 | 1/2007 |
| WO | 2007038350 | 4/2007 |
| WO | 2007040750 | 4/2007 |
| WO | 2007040888 | 4/2007 |
| WO | 2007041702 | 4/2007 |
| WO | 2007053566 | 5/2007 |
| WO | 2007060534 | 5/2007 |
| WO | 2007075454 | 7/2007 |
| WO | 2007081849 | 8/2007 |
| WO | 2007087469 | 8/2007 |
| WO | 2007087628 | 8/2007 |
| WO | 2007090021 | 8/2007 |
| WO | 2007092056 | 8/2007 |
| WO | 2007092870 | 8/2007 |
| WO | 2007097905 | 8/2007 |
| WO | 2007109470 | 9/2007 |
| WO | 2007114834 | 10/2007 |
| WO | 2007118045 | 10/2007 |
| WO | 2007121030 | 10/2007 |
| WO | 2007121057 | 10/2007 |
| WO | 2007121271 | 10/2007 |
| WO | 2007123920 | 11/2007 |
| WO | 2007124222 | 11/2007 |
| WO | 2007124249 | 11/2007 |
| WO | 2007127595 | 11/2007 |
| WO | 2007127604 | 11/2007 |
| WO | 2007130835 | 11/2007 |
| WO | 2007130941 | 11/2007 |
| WO | WO 2007130840 | 11/2007 |
| WO | 2007138270 | 12/2007 |
| WO | 2007146032 | 12/2007 |
| WO | 2008005740 | 1/2008 |
| WO | 2008006098 | 1/2008 |
| WO | 2008008511 | 1/2008 |
| WO | 2008013892 | 1/2008 |
| WO | 2008027860 | 3/2008 |
| WO | 2008033742 | 3/2008 |
| WO | 2008036975 | 3/2008 |
| WO | 2008039777 | 4/2008 |
| WO | 2008051737 | 4/2008 |
| WO | WO 2008037256 | 4/2008 |
| WO | WO 2008042948 | 4/2008 |
| WO | WO 2008048923 | 4/2008 |
| WO | WO 2008048953 | 4/2008 |
| WO | WO 2008069420 | 5/2008 |
| WO | 2008070716 | 6/2008 |
| WO | 2008134703 | 6/2008 |
| WO | 2008078163 | 7/2008 |
| WO | 2008082737 | 7/2008 |
| WO | WO 2008100590 | 8/2008 |
| WO | 2008124772 | 10/2008 |
| WO | WO 2008118295 | 10/2008 |
| WO | WO 2008119006 | 10/2008 |
| WO | 2008140756 | 11/2008 |
| WO | 2008157589 | 12/2008 |
| WO | 2009003153 | 12/2008 |
| WO | 2009006225 | 1/2009 |
| WO | 2009011845 | 1/2009 |
| WO | 2009014540 | 1/2009 |
| WO | 2009015100 | 1/2009 |
| WO | 2009018086 | 2/2009 |
| WO | 2009029928 | 3/2009 |
| WO | 2009055028 | 4/2009 |
| WO | 2009055400 | 4/2009 |
| WO | 2009055407 | 4/2009 |
| WO | 2009152302 | 12/2009 |
| WO | 2009155360 | 12/2009 |
| WO | 2010017631 | 2/2010 |
| WO | 2010018316 | 2/2010 |
| WO | 2010018317 | 2/2010 |
| WO | 2010019857 | 2/2010 |
| WO | 2010030916 | 3/2010 |
| WO | 2010045383 | 4/2010 |
| WO | 2010065648 | 6/2010 |
| WO | 2010078901 | 7/2010 |
| WO | 2010111500 | 9/2010 |
| WO | 2010120989 | 10/2010 |
| WO | 2010147639 | 12/2010 |
| WO | 2011043805 | 4/2011 |
| WO | 2011068818 | 6/2011 |
| WO | 2012033532 | 3/2012 |
| WO | 2012075827 | 6/2012 |
| WO | 2012088890 | 7/2012 |

OTHER PUBLICATIONS

CD Horizon M8 Multi Axial Screw Spinal System Brochure, Medtronic Sofamor Danek, no publish date.
Claris Instrumentation Brochure, G Med, pub. 1997.

(56) References Cited

OTHER PUBLICATIONS

Contour Spinal System Brochure, Ortho Development, no publish date.
EBI Omega 21 Brochure, EBI Spine Systems, pub. 1999.
SDRS Surgical Dynamics Rod System Brochure, Surgical Dynamics, pub. 1998-99.
Silhouette Spinal Fixation System Brochure, Sulzer Medica Spine-Tech, no publish date.
Spine, Lipcott, Williams & Wilkins, Inc. vol. 24, No. 15, p. 1495.
The Moss Miami 6.0mm System Advertisement, author unknown, no publish date.
The Rod Plate System Brochure, Stryker Howmedica Osteonics, pub. Oct. 1999.
The Strength of Innovation Advertisement, Blackstone Medical Inc., no publish date.
Versalok Low Back Fixation System Brochure, Wright Medical Technology, Inc., pub. 1997.
VLS System Variable Locking Screw Brochure, Interpore Cross International, 1999.
Xia Spinal System Brochure, Stryker Howmedica Osteonics, no publish date.
Brochure of DePuySpine on Surgical Technique, Published 2004, pp. 1-36.
European Search Report, EP14189707.4, dated Feb. 25, 2015.

BONE ANCHOR CLOSURE PIVOT-SPLAY CONTROL FLANGE FORM GUIDE AND ADVANCEMENT STRUCTURE

CROSS-REFERENCE TO RELATED APPLICATIONS

This application claims the benefit of U.S. Provisional Patent Application Ser. No. 61/920,033, filed Dec. 23, 2013, which is incorporated by reference herein. This application is a continuation in part of U.S. patent application Ser. No. 14/569,142, filed Dec. 12, 2014, which claims the benefit of U.S. Provisional Patent Application Ser. No. 61/915,085, filed Dec. 12, 2013 which are each incorporated by reference herein.

BACKGROUND OF THE INVENTION

The present invention is directed to structure for joining together parts of a medical implant, in particular for use with open bone anchors in spinal surgery, and in some embodiments thereof, for use with spinal bone anchors such as polyaxial screws having upwardly extending arms with helically wound guide and advancement structures.

Bone anchors, such as bone screws and hooks, are utilized in many types of spinal surgery in order to secure various implants to vertebrae along the spinal column for the purpose of stabilizing and/or adjusting spinal alignment. For example, the most common mechanism for providing vertebral support is to implant bone screws into certain bones which then in turn support a longitudinal connecting member, such as a rod connector, or are supported by the connector. Although both closed-ended and open-ended bone anchors are known, open-ended anchors are particularly well suited for connections to longitudinal connecting members such as hard, soft or deformable rods, dynamic, soft or elastic connectors and connector sleeves or arms, because such rods or other connector members do not need to be passed through a closed bore, but rather can be laid or urged into an open channel within a U-shaped receiver or head of such a bone anchor. Generally, the anchors must be inserted into the bone as an integral unit or a preassembled unit, in the form of a shank or hook and connected pivotal receiver. In some instances, a portion of such a preassembled unit, such as a shank of a polyaxial bone screw assembly, may be independently implanted into bone, followed by push- or pop-on assembly of a receiver portion of the unit that includes the open channel for receiving a rod connector or other longitudinal connecting member.

Typical open-ended bone screws include a threaded shank with a head or receiver having a pair of parallel projecting branches or arms which form a yoke with a U-shaped slot or channel to receive a portion of a rod or other longitudinal connecting member. Hooks and other types of connectors, as are used in spinal fixation techniques, may also include similar open ends for receiving rods or portions of other fixation and stabilization structure. After the rod or other longitudinal connecting member is placed in the receiver channel, a closure, typically in the form of a substantially cylindrical plug is often used to close the channel. Known closures include slide-on types, twist-on varieties that are rotated ninety degrees to a locked in position, and a variety of single start helically wound guide and advancement structures including, for example, thread forms having v-thread, reverse-angle, buttress or square thread forms, to name a few, as well as other non-threadlike helically wound forms, such as helical flanges.

It is known that the angled loading flank of a v-thread closure generates outward splay of spaced open implant receiver arms at all loading levels without limit. Thus, v-threaded closures or plugs are sometimes used in combination with outer threaded nuts that prevent outward splaying of the receiver arms. To overcome the splay problems of v-threaded closures, so-called "buttress" thread forms were developed. In a buttress thread, the trailing or thrust surface is linear and oriented somewhat downwardly in the direction of advancement with respect to the thread axis, while the leading or clearance surface is angled rearwardly in varying degrees, theoretically resulting in a neutral radial reaction of a threaded receptacle or receiver to torque on the threaded closure member being received thereby. In reverse angled thread forms, which theoretically positively draw the threads of a receptacle radially inwardly toward the thread axis when the reverse angle closure thread is torqued, provided the outer tip of the thread is crested and strong enough, the trailing linear surface of the external thread of the closure is angled somewhat upwardly toward the thread axis instead of away or somewhat downwardly from the thread axis (as in conventional v-threads). Although buttress and reverse angle threads with linear loading surfaces reduce the tendency of bone screw receiver arms to splay outwardly, they are not structured to control it and the arms may still be flexed outwardly by bending moment forces acting on the implant arms and the closure threads can be bent, deformed or even sheared off by forces exerted during installation, as well as experienced post-operatively on the implants with certain activities.

Closures made with square threads, again, having linear loading surfaces, theoretically keep all forces axially directed. However, it has been found that under a moderate load, square thread closures produce a marginal splay and under heavy load, splay can be considerable, indicating that traditional square thread machine design theories directed to power screws and other screws for use in substantially closed bores do not adequately describe and reflect the environment of a spinal open bone screw receiver having a relatively small size with spaced apart arms in lieu of a bore. Furthermore, square threaded spinal bone anchor closures have been shown to experience heretofore unexplained and undesirable excess stress concentrated on their upper outer loading flank portions located near the crest of the thread believed by Applicants to be due to outwardly directed rotational pivot and displacement of the mating receiver arm thread flank portions when under the stress of loading between the arms of an open receiver. This occurs during intra-operative tightening and post-operative physiologic loading, which is believed to have resulted in in-vivo loosening in some cases.

SUMMARY OF THE INVENTION

A spinal implant closure structure embodiment according to the invention that includes a closure structure or plug mated with opposed arms of an open bone anchor includes splay allowance and splay arresting surfaces for holding a spinal fixation longitudinal connecting member, such as a rod, the anchor having an open receiver with spaced apart arms defining a longitudinal connecting member receiving channel therebetween. Embodiments of the present invention provide distinct dissimilar mating guide and advancement flange forms on the closure and cooperating receiver arms to allow, but ultimately control pivot splay of the arms when the closure is rotated and advanced between the arms and thereafter tightened, and wherein adequate and desired locking thrust is generated in so doing. Specifically, embodiments of the invention initially allow for some splay that has been found to reduce torque and improve thrust during initial loading of the closure into the receiver arms and then aid in splay control during torquing or tightening of the closure with respect to the arms that occurs when the closure abuts against an insert located in the receiver or directly against a longitudinal connecting member.

According to an aspect of the invention, the closure flange form includes a first portion located adjacent a root of the form and extending radially outwardly therefrom in a direction away from the central axis, the first portion having a first load flank surface that terminates at a first splay control ramp having another surface sloping upwardly and outwardly at some predetermined angle. A discontinuous receiver flange form second load flank surface is configured to form an acute angle with the closure first load flank surface and engage the closure first load flank at a vertex of such acute angle, the vertex being located substantially medial of the closure splay control ramp. Stated in another way, the closure flange form first load surface and cooperating bone anchor receiver flange form second load surface are configured to be oriented at least initially toward one another in a non-parallel contact relationship early in the loading and tightening process with such contact initially located near the closure root surface. When the closure is tightened against a rod or other bone anchor feature later in an assembly process, the location of contact between the closure load surface and the receiver load surface may migrate slightly toward the closure flange form crest, but remains close to the closure root with the acute angle between the load surfaces reducing slightly due to pivot splay occurring in the upright arms of the receiver. Radially outward portions of the load flanks remain spaced from one another even when the closure is tightly fixed to the bone anchor. The closure flange form also has a second portion extending radially outwardly from a termination of the load flank to a crest of the flange form. The second portion includes the first splay control ramp and a raised toe that can be contoured or rounded, and which has an upper surface that remains unloaded in use, the toe being spaced from the first load flank both radially and axially.

The discontinuous receiver guide and advancement flange form extends helically about and along an inner surface of each receiver arm, the receiver flange form having the second load flank and a second splay control ramp. The second load flank engaging the first load flank at an angle as set forth above and the second splay control ramp ultimately engaging the first splay control ramp to arrest outward receiver arm rotational splay, the receiver flange form having clearance surfaces disposed in close spaced relation to a remainder of the closure flange form. Thus, the receiver arm flange forms are not typically identical in shape and size to the closure flange form. For example, if the closure load flank is substantially horizontal, the cooperating receiver load flank is oriented at a slight reverse angle. If, however, the closure load flank slopes in a downward and outward direction from the closure root, then the receiver load flank may be oriented generally horizontally. Likewise, if the closure load flank slopes upwardly and outwardly from the closure root, the cooperating receiver load flank may be further undercut to provide an angle of inclination between the two loading surfaces to accommodate an acceptable amount of outward splaying of the receiver arms that also includes an outward pivot of the arms which is identified herein by the term "pivot-splay." Because the closure and receiver loading flanks are always at an acute angle to one another, contact between the loading flanks remains close to the closure root during pivot-splay of the receiver arms. At an acceptable level of receiver pivot-splay, the splay control ramps of the closure and receiver engage, arresting any further undesirable pivot-splay of the receiver arms and the loading flanks can be slightly more parallel with respect to each other.

Other aspects of the invention include sizing the closure flange form to capitalize on tensile forces by reducing flange form depth and variable sizing of the closure unloaded toe to strengthen the closure mechanism.

Objects of the invention further include providing apparatus and methods that are easy to use and especially adapted for the intended use thereof and wherein the tools are comparatively inexpensive to produce. Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

Figure 1:
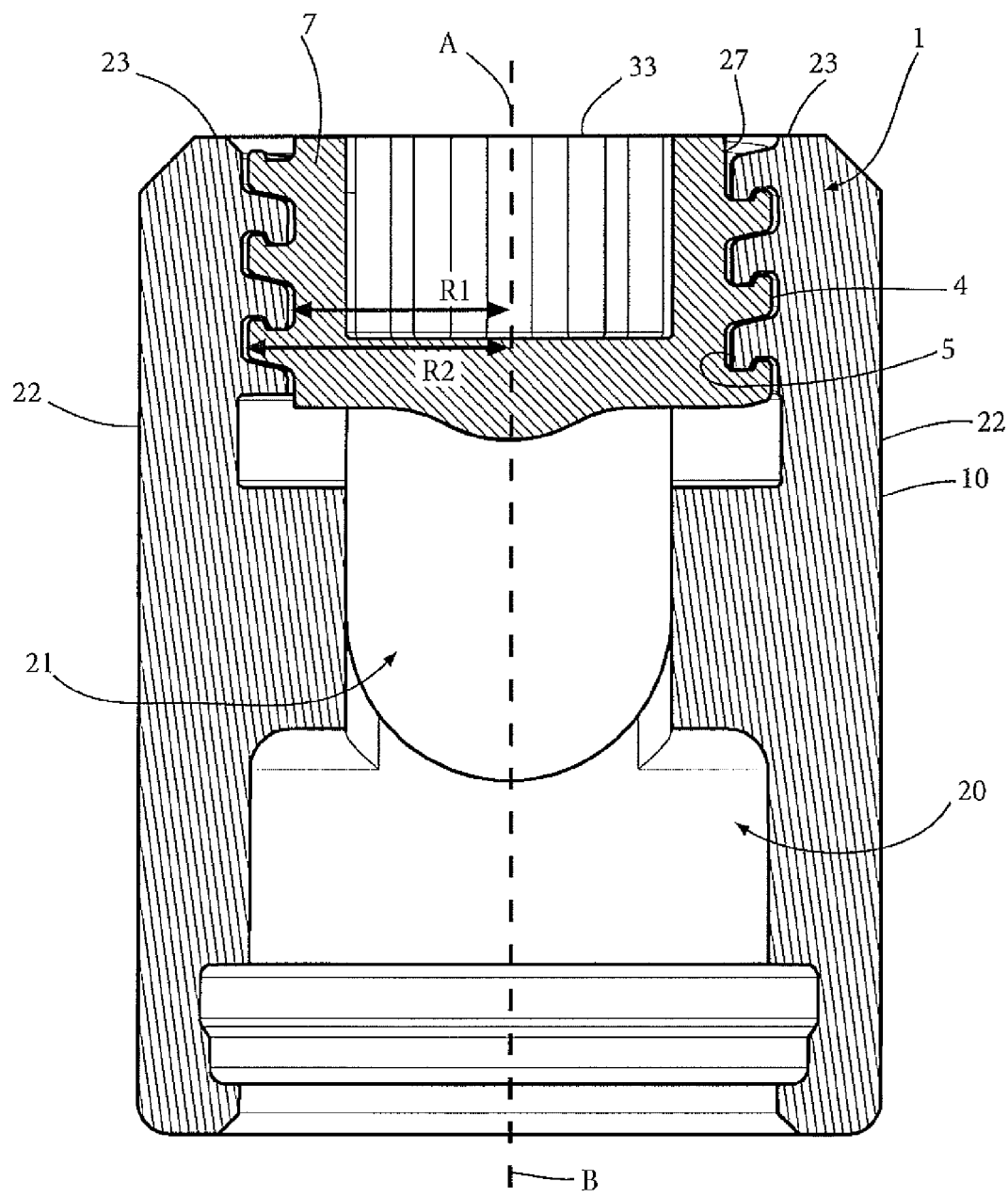
FIG. 1 is a front elevational view of a portion of a spinal implant showing only a rod receiver and a closure and with portions broken away to show the detail of a closure flange form mechanism according to an embodiment of the invention.

As required, detailed embodiments are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the bone attachment structures in actual use.

It is noted that helically wound pivot-splay accommodating and controlling flange forms described in detail herein cannot be considered thread forms as flange forms include numerous features, including surfaces and contours, some which may be compound and non-linear, in addition to and not anticipated by traditional screw thread technology and nomenclature. However, certain terms used in this application will be similar to those used in thread form nomenclature. For example, in traditional v-thread nomenclature, a flank is often described as a thread face running from a root to a crest of a thread form with the root being the bottom surface joining flanks of two adjacent flanks and the crest being the top and bottom surfaces joining two flanks of a single thread form near an outer edge or tip thereof. In this application, the term flank may be used to describe certain surfaces of a flange form, such as a loading or thrust surface, but unlike a thread, a flange form flank does not necessarily connect a root to a crest of a particular form. Similarly, a crest or outermost edge surface of a flange form does not necessarily function as the surface that joins two flanks as other features, such as splay control surfaces and/or unloaded curves or contours, may be located between a flank and a crest. Furthermore, while a root surface of a flange form may typically be substantially cylindrical and a crest surface of a flange form may be at least partially cylindrical, such surface may also be sloped or curved. Thus, an entire outer surface which might be identified as a "crest" surface of a closure plug may or may not be at a uniform distance from a cooperating root surface.

Also, the terms lead, pitch and start, as such terms are used to describe other helically wound guide and advancement structures, are to be understood as follows: Lead is a distance along the axis of a closure or plug that is covered by one complete rotation (360 degrees) of the closure with respect to a mating structure. Pitch is the distance from a location on a crest or most outward surface of one flange form structure to the same location on the next or adjacent flange form. For example in a single-start thread-form, such as a single start, helically wound v-thread closure plug, lead and pitch are the same. Single start means that there is only one helically wound form wrapped around a cylindrical core, or in the case of embodiments of closures according to the present invention, wrapped around a cylindrical closure plug body and thus there is only one start structure or surface at a base or forward end of the closure body that initially engages a mating structure on an open implant. Each time a single start closure rotates one turn (360 degrees), the closure has advanced axially by a width of one helical flange form. Double-start means that there are two forms wrapped around a core body and thus there are two starting surfaces or structures on the closure plug. Therefore, each time a double-start body rotates one turn (360 degrees), such a body has advanced axially by a width of two helical flange forms. Multi-start means that there are at least two and may be up to three or more of such forms wrapped around a core body. Similar to threads, flange forms may also be coarse or fine. Course flange forms are those with a larger pitch (fewer forms per axial distance) and fine forms have a smaller pitch (more forms per axial distance).

With particular reference to FIGS. 1-5, the reference numeral 1 generally indicates a closure mechanism in accordance with an embodiment of the invention that includes a male helical flange form, generally 4, rotatingly mated with a female helical flange form, generally 5. The form 4 is located on a bone implant closure 7 and the form 5 is located on opposed arms of an open bone anchor receiver 10. The receiver 10 is further part of a polyaxial bone screw apparatus or assembly that includes a shank (not shown) with a body having a bone engaging and implantation thread and also an upwardly extending substantially or partially spherical upper portion or head some or most of which may or may not be integral to the shank body. The receiver 10 has a cavity or inner chamber, generally 20, for receiving such a shank head, the cavity 20 communicating with an upper rod receiving channel, generally 21, formed between opposed arms 22 having top surfaces 23. The discontinuous flange form 5 is located near the top surface 23 of each arm 22 and faces inwardly toward the channel 21, winding helically downwardly in a direction toward the cavity 20 and thus defining an upper portion of the channel 21.

The illustrated closure 7 is a single piece structure with the flange form 4 having a single start and having an axis of rotation A. The closure top 7 mates under rotation with the receiver 10 having a central axis B with the axis A being aligned with the axis B. Closures according to the invention may take a variety of forms, including single and multi-start options, one piece closures, two piece closures, closures with break-off heads, closures with cannulation bores, for example, and may be used with a wide variety of medical implants, including, but not limited to mono-axial screws and hooks, hinged or uni-planar screws and hooks and dual multi-piece polyaxial bone screws and hooks, as well as screws with sliding or pivoting inserts. A variety of polyaxial bone screws may also be used with splay control structures of the invention and the illustrated embodiment should not be considered limiting. For example, splay control structures of the invention may be used with bone screws having top loaded bone screw shanks with spherical heads and also with bottom-loaded multi-part screw shanks as well as bottom loaded push or "pop-on" screws, such as Applicant's U.S. patent application Ser. No. 12/924,802, filed Oct. 5, 2010, for example, that is incorporated by reference herein. The closure 7 ultimately frictionally engages and presses against a longitudinal connecting member, for example, a rod connector (not shown), so as to capture, and fix the longitudinal connecting member within the receiver 10 and thus fix the member relative to a vertebra (not shown). The rod is typically hard, stiff, non-elastic and cylindrical, having an outer cylindrical surface. However, a longitudinal connecting member for use with bone anchors having the closure mechanism 1 may take the form of an elastic or deformable rod or have a different cross-sectional geometry. The longitudinal connecting member may also be a part of a soft or dynamic system that may include hard or soft structure for attaching to a bone anchor and may further include a tensioned cord, elastic bumpers and spacers located between bone screws, for example. In polyaxial embodiments, such as those illustrated in U.S. patent application Ser. No. 12/924,802, previously incorporated by reference herein, the receiver 10 and the shank cooperate in such a manner that the receiver 10 and the shank can be secured at any of a plurality of angles, articulations or rotational alignments relative to one another and within a selected range of angles both from side to side and from front to rear, to enable flexible or articulated engagement of the receiver 10 with the shank until both are locked or fixed relative to each other near the end of an implantation procedure.

With particular reference to FIGS. 2-5, the illustrated single-start closure 7 outer splay accommodating and control structure or flange form 4 operably joins with mating flange form structure 5 disposed on the arms 22 of the receiver 10 to result in the interlocking guide and advancement structure or arrangement, generally 1. Although one particular flange form structure and relationship, generally 1, will be described herein with respect to the forms 4 and 5, it is noted that there are a variety of flange form geometries, including, for example, those described in Applicant's U.S. patent application Ser. No. 11/101,859 filed Apr. 8, 2005 (US Pub. No. 2005/0182410 published Aug. 18, 2005), which is incorporated by reference herein as helpful background.

Each form 4 includes several surfaces or contours that helically wrap about the axis A. The contours of the flange form 42 include a root surface 27 that is helical and disposed substantially parallel to the axis A. A virtual cylinder formed by the root surface 27 has a radius R1 (radial distance between the axis A and the surface 27). Adjacent the root surface 27 is a radiused surface, curve or corner surface 28 that in turn is adjacent to a load or loading surface or flank 29. The load flank 29 is on a trailing side relative to a direction of advancement of the structure 4 along the receiver axis B when the structure 4 rotatingly mates with the flange form 5 on the receiver arms 22. In the illustrated embodiment, the load flank 29 also slopes slightly downwardly in a direction running radially outwardly from the root surface 27 toward an outer or crest surface 31 as indicated by a line F1 on FIG. 2. However, the load flank 29 does not extend all of the way to the crest surface 31 as will be described in greater detail below. In some embodiments of the invention, the load flank 29, or at least portions thereof, may slope more steeply with respect to the horizontal, may be substantially horizontal (i.e., perpendicular to the axis A) or may even slope in a slightly upward direction toward a top surface 33 of the closure structure 7, i.e., reverse angle in nature. As will be discussed in more detail below, whatever the angular of orientation of the load flank 29 of the closure 7, an angular orientation of a cooperating adjacent load flank of the receiver 10 (indicated by a line F2 on FIG. 2) will be configured such that the opposing closure and receiver load flanks are in a non-parallel relationship so as to accommodate for pivot and thread tilt that occurs with receiver 10 arm pivot-twist-splay during rotational mating of the closure 4 within the receiver 10, setting an initial contact between the closure and receiver loading flanks at a position substantially medially on the male closure flank; in other words at a position at or close to the radiused surface 28 that transitions between the root surface 27 and the loading flank 29 of the closure flange form 4 (see, e.g., FIG. 5). It is noted that the downwardly sloping load flank 29 may actually cause some initial outward splay of the arms 22 during rotation of the form 4 into the form 5 which may be desirable as such an outward splay of the receiver arms 22 reduces torque and thus improves thrust of the closure 7 as it is driven into the receiver 10.

In certain embodiments, as is shown in the present illustration, a substantial portion of the crest surface 31 is substantially parallel to the root surface 27. Thus, a virtual cylinder formed by the crest surface 31 has a radius R2 (radial distance between the axis A and the surface 31). However, in other embodiments, the outer or crest surface may include radiused surfaces at a top and bottom thereof and may further have other sloping portions that are not parallel to the root surface. Thus, although the radial measurements R1 and R2 are substantially uniform for the illustrated embodiment, it is noted that in other embodiments, R1 would refer to the smallest distance from the axis A to a root surface or point 27 and R2 would refer to the greatest distance between the axis A and a crest surface or point 31. Furthermore, a distance D identifies a depth of the flange form 4 from the crest 31 to the root 27. Stated in another way, D=R2−R1. The distance or depth D may be further broken down into D1 and D2 wherein D1 is a distance from the crest surface 31 to the load flank 29 and D2 is a length of the load flank 29 measured from the root surface 27 to a location where the load flank 29 terminates. The distance D1 can be equal to, less than or greater than D2. The distance or depth D2 may preferably range from between about forty to about sixty percent of the total distance D.

Adjacent the loading flank 29 and running upwardly (in a direction toward the top surface 33) as well as outwardly toward the crest surface 31, is a splay control ramp or surface portion, generally 35 that in the illustrated embodiment includes a lower substantially frusto-conical surface 36 and an upper convex radiused surface portion 37. It is noted that although the splay control ramp 35 is ultimately an "anti-splay" structure for interlocking with the flange form 5 on the receiver arms 22, prohibiting undesirable outward splay of the arms 22 when in full locking engagement with the closure structure 7, it has been found that some limited splay and pivoting of the receiver arms 22 typically occurs and is even desirable as the splay beneficially reduces torque and desirably improves thrust during early loading of the closure into the receiver, but the splay control ramp advantageously arrests or limits such pivot-splay to a desired, acceptable amount.

In the illustrated embodiment, the radiused surface 37 is adjacent to another radiused surface 40 that curves outwardly and then downwardly, converging into the crest surface 31. The splay control ramp surfaces 36 and 37 and the upper rounded or radiused surface 40 define a protrusion, bead or toe, generally 41, of the flange form 4 that is directed generally upwardly toward the top surface 23 and is located outwardly away from the loading flank 29 and opposite a downward or leading facing heel or stab flank 42 of the form 4. The surfaces defining the toe 41 are spaced from the load flank 5, and, unlike the load flank 29, the toe 41 is never loaded, but always spaced from the flange form 5 of the receiver 10. It is noted that the load flank 29 may also be referred to as a thrust surface while the stab flank 42 may also be referred to as a clearance surface. To complete the illustrated flange form 4 geometry, a curved surface 46 made up of one or more radiused surface portions joins the stab surface 42 to the root surface 27.

Figure 4:
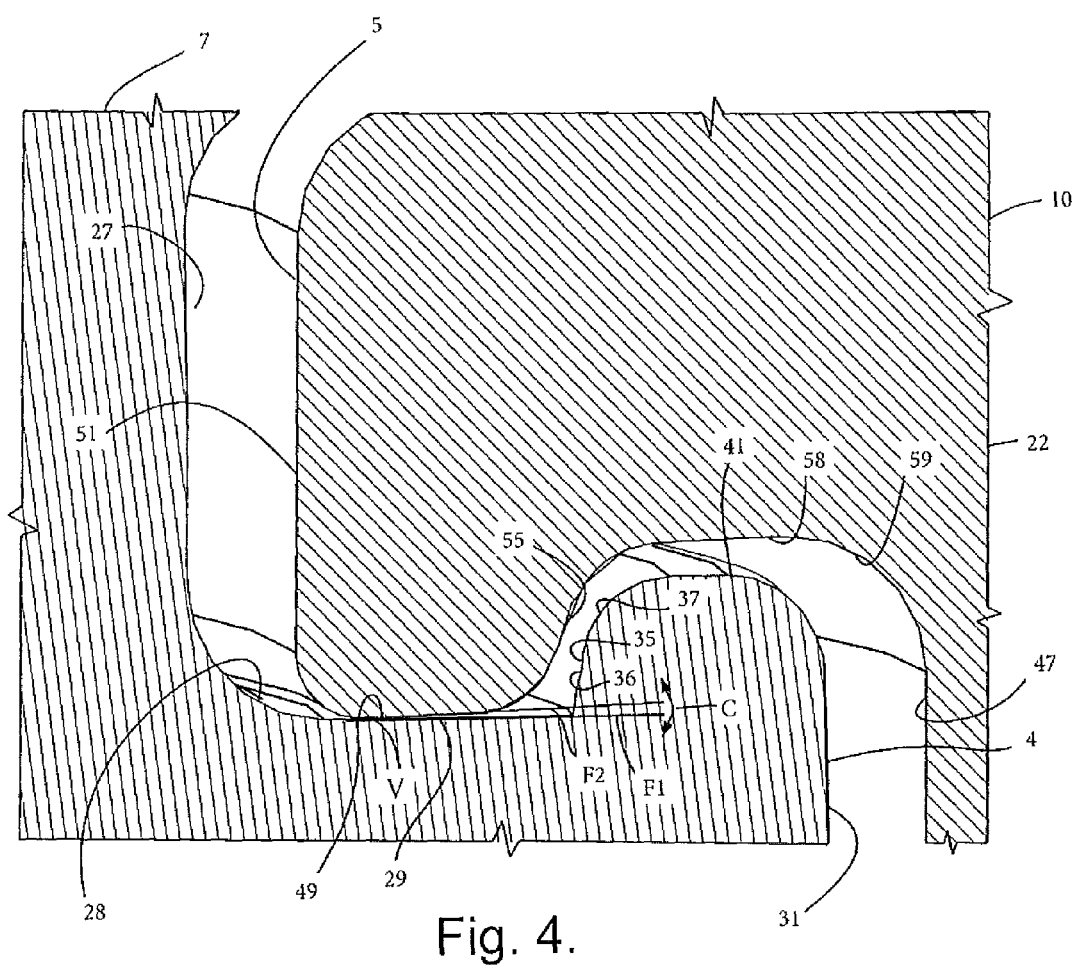
FIG. 4 is another enlarged and partial front elevational view with portions broken away of the closure flange form mechanism of FIG. 1 shown in an early mating and loading stage of assembly.
Figure 5:
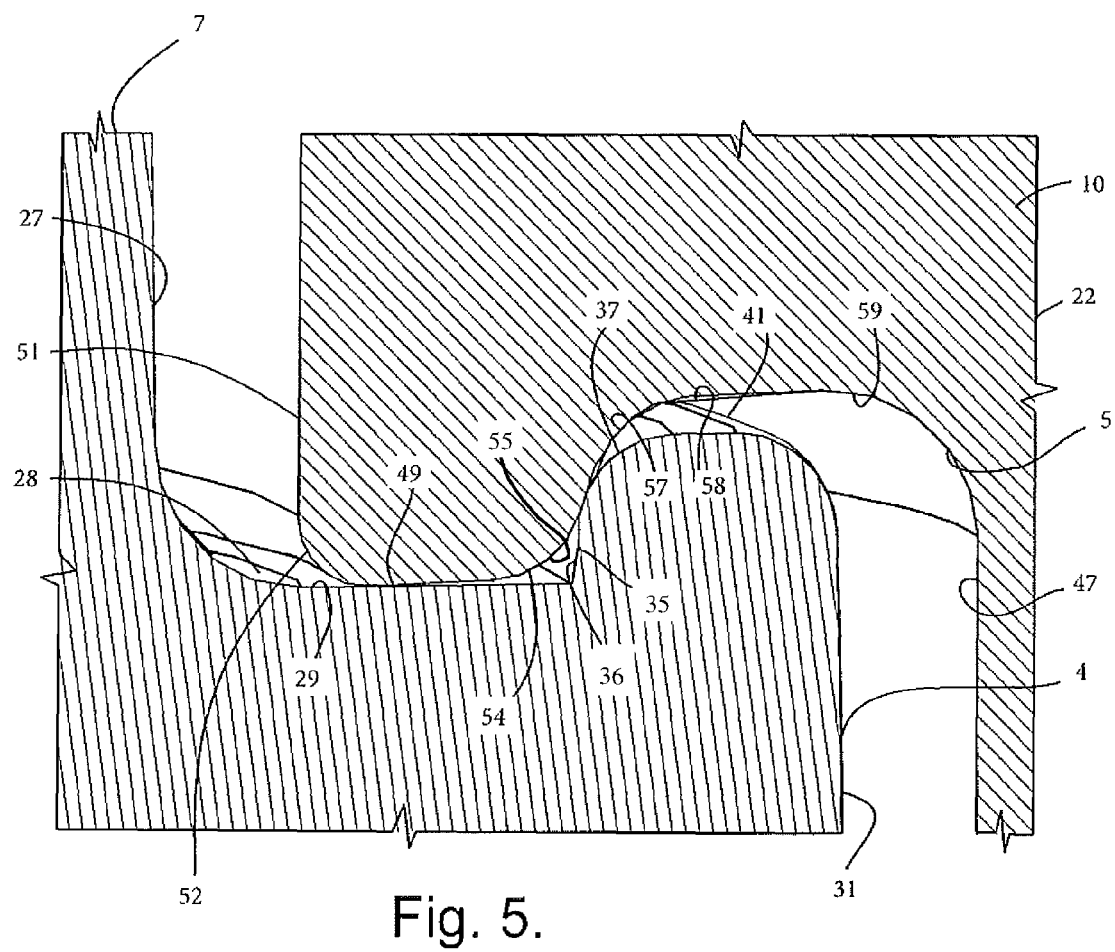
FIG. 5 is another partial front elevational view with portions broken away of the closure flange form mechanism of FIG. 4 shown in a subsequent tightening stage of assembly.

The discontinuous flange form 5 located on each receiver arm 22 cooperates with the form 4, but is not identical thereto or even a mirror image thereof. Rather, a balance is created between the flange form 4 and the flange form 5 to provide load and clearance surfaces to result in a desired splay control of the receiver arms 22. Also, cooperating loading flanks of the forms 4 and 5 are configured to allow for a desired amount of receiver pivot-splay during loading of the closure 4 into the receiver 10 and cooperating splay control ramps are configured to ultimately limit receiver pivot-splay during tightening of the closure 4 within the receiver 10. The flange form 5 includes a root surface 47, a load flank 49 and a crest surface 51. A radiused corner surface 52 connects the flank 49 and the crest surface 51. At an opposite side of the load flank 49 a radiused surface 54 joins the flank 49 with a splay control ramp 55. The splay control ramp 55 terminates at a location 57 that is adjacent a clearance surface 58 that extends toward the root surface 47. Another radiused surface 59 connects the clearance surface 88 with the root surface 47. At an opposite side of the root surface 47, another radiused corner surface 60 connects the root surface 47 with a stab flank or surface 64. To complete the geometry of the flange form 5, a radiused corner surface 65 connects the stab flank 64 with the crest surface 51. The flange form 5 load flank 49 frictionally engages the closure form 4 load flank 29. Unlike the closure form 4 toe 41 that does not engage the form 5 and thus is never loaded, the load flank 49 of the receiver flange form 5 may be identified as a loaded toe. Thus, although the flange form 4 looks very much like the flange form 5, similar geometric forms do not perform similarly. As is also shown in FIGS. 4 and 5, the splay control ramp 55 of the flange form 5 engages the splay control ramp 35 of the flange form 4 when the closure structure 7 is mated and torqued into tight locking engagement with the form 5 on the receiver arms 22.

In general, the load flanks 29 and 49 are positively engaged and axially loaded, that is, loaded in the direction of the axis A and axis B, when the closure 7 is advanced into the receiver arms 22. As relative torque between the closure 7 and the arms 22 increases by engagement with an insert or by engagement with a clamped member such as a rod connector, there is a tendency for the arms 22, to not only splay outwardly away from the axis A, but to also rotate and pivot outwardly. For example, see FIG. 3 that illustrates an outward pivot of the receiver arms 22 indicated by the arrow P. It is believed that a center of rotation X of the splay is located within each receiver upright arm 22 and would create unfavorable loading conditions for the closure flange form 4, placing additional stress as well as outward displacement on the closure load flank 29 if the receiver load flank 49 is configured to mate in a substantially parallel and flush manner with the flank 29. However, as illustrated by the extended lines F1 (runs along the load flank 29) and F2 (runs along the load flank 49) in FIG. 2, for example, the illustrated closure load flank 29 is disposed at an acute angle with respect to the load flank 49 of the receiver flange form 5. With particular reference to FIG. 4, during rotational mating of the closure 7 within the receiver 10 but prior to further loading or tightening, the receiver load flank 49 initially engages the closure load flank 29 in an non-parallel relationship, making contact at a location at or near the closure radiused surface 28 that is adjacent the closure root surface 27. Stated in another way, the discontinuous receiver thread form load flank surface 49 (see the extended line F2) is configured to form an acute angle with the closure load flank surface 29 (see the extended line F1) and engage the closure load flank 34 at a vertex V of an acute angle formed by a contact point of the surfaces 29 and 49, such vertex V being located substantially medial of the closure splay control ramp 35. As a practical matter, the initial point of contact V between the surfaces 29 and 49 (e.g., the acute angle vertex V) should not be located at the closure root surface 27, but rather at or substantially near where the radiused inner corner surface 28 terminates and transitions into the load flank surface 29 as best shown in FIG. 4. With reference to FIG. 5, as the closure 7 is tightened against an insert located within the receiver 10 or directly against a rod connector and the receiver arms 22 experience some outward pivot-splay, a load bearing line or patch of contact may move slightly outwardly away from the radiused surface 28, but remain substantially medial of the closure splay control ramp. FIG. 5 also shows that upon tightening, contact between the splay control ramps 35 and 55 arrests any further pivot-splay of the receiver arms 22. Thus, limited outward pivot-type splay of the receiver arms 22 may occur without unfavorably pre-loading outward portions of the thread 4 of the closure 7 located near the splay control ramp 35. During the rotating and tightening of the closure 7 within the receiver 10, the closure toe 41 remains unloaded and radially outer portions of both load flanks 29 and 49 remain spaced from one another. In the illustrated embodiment translation of the contact line or patch between the load flanks 29 and 49 undergo an outward translation of about one-half the total splay of the receiver arms 22, which typically spread apart about 0.004 to about 0.006 inches. Thereafter, the splay control ramps 35 and 55 mutually engage in a radial direction to interconnect and mechanically lock, resisting any further splaying tendency of the receiver arms 22 for example, in FIG. 3, by the lines Y (along the closure root surface 27) and Z (along the receiver crest 51).

Figure 2:
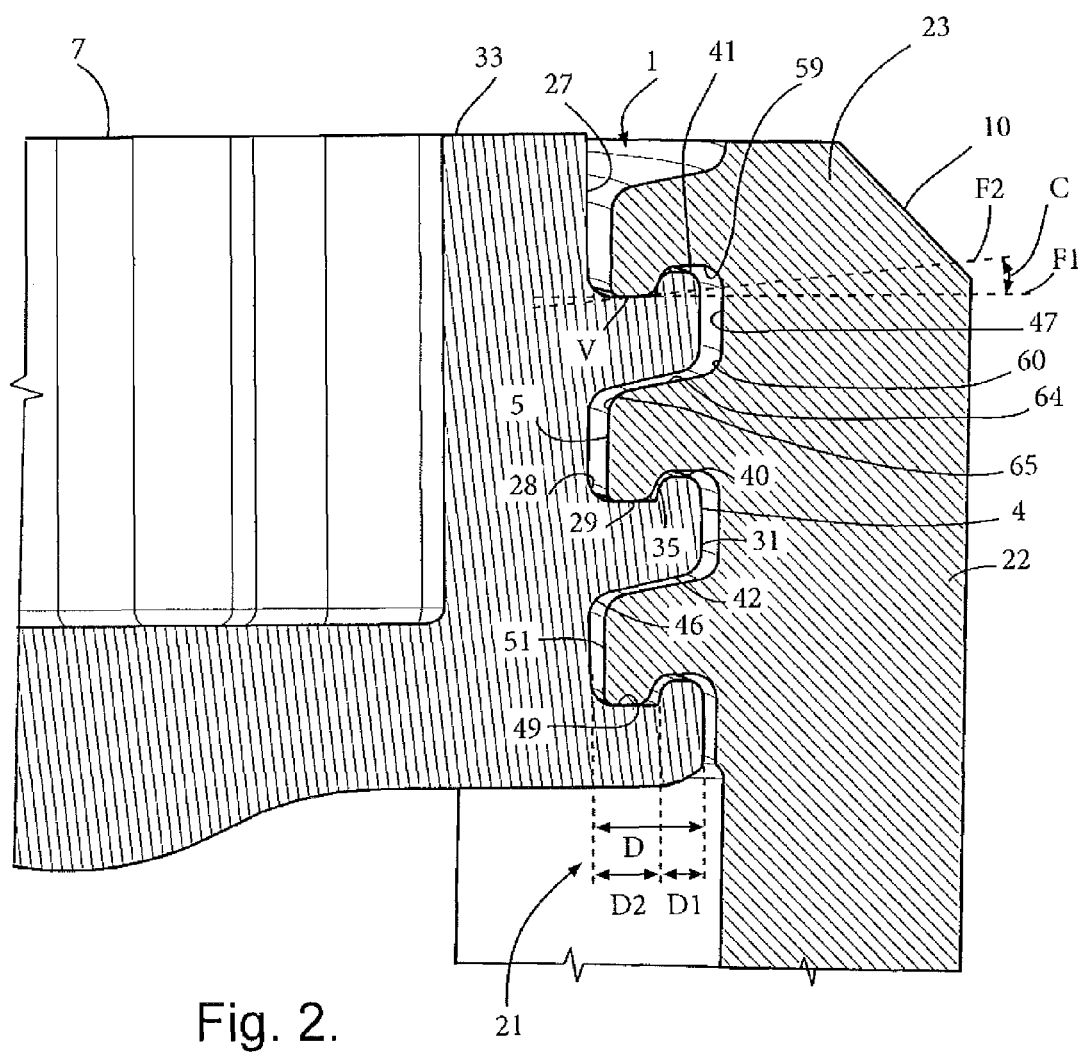
FIG. 2 is an enlarged and partial front elevational view with portions broken away of the closure flange form mechanism of FIG. 1.
Figure 3:
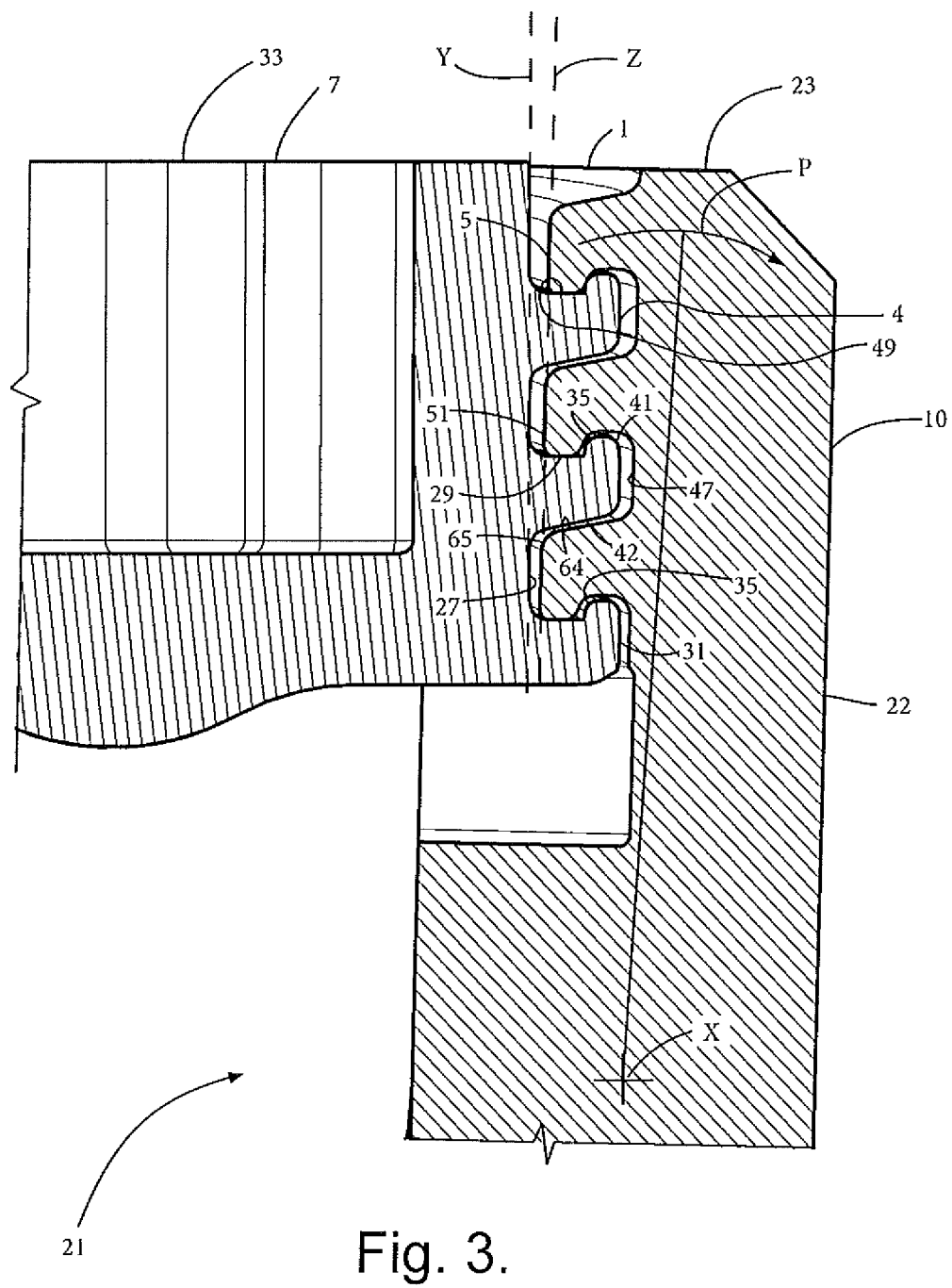
FIG. 3 is another enlarged and partial front elevational view with portions broken away of the closure flange form mechanism of FIG. 1.

As described previously herein, FIGS. 1-6 illustrate the closure 4 and receiver 10 wherein the closure load flank 29 (see extension reference line F1) slopes downwardly and the receiver load flank 49 (see extension reference line F2) is disposed substantially horizontally and such lines intersect at a vertex V at an angle C. With particular reference to FIGS. 2, 4, and 5, it is noted that the angle C decreases slightly, or in some instances, does not substantially change during loading and tightening of the closure 7 within the receiver 10. Rather, a moving contact patch defined in part by the vertex V migrates outwardly a minimal amount, but remains close to the closure root surface 27. The angle C is to accommodate receiver arm pivot (each arm 22) of about one to two degrees, preferably between about 1.2 and about 1.4 degrees for each receiver arm 22 followed by a stop or check of the receiver pivot-splay by engagement of the splay control ramps 35 and 55. Torque applied is generally about 75 to about 90 inch pounds with the illustrated flange forms 4 and 5. Thread pitch can vary, but preferably ranges between about 0.039 inches and about 0.045 inches for smaller flange forms, with larger pitches for larger flange forms.

It is noted that in other embodiments of the invention, as long as an angle C is formed between the load flanks 29 and 49, the flanks need not be in the configuration shown in FIGS. 1-5. For example, the closure load flank 29 could be substantially horizontal and perpendicular to the closure axis A and the receiver load flank 49 could have a reverse angle or undercut. Furthermore, the closure load flank 29 could slope upwardly, requiring a further undercut or greater reverse angle orientation of the receiver load flank 49.

Figure 6:
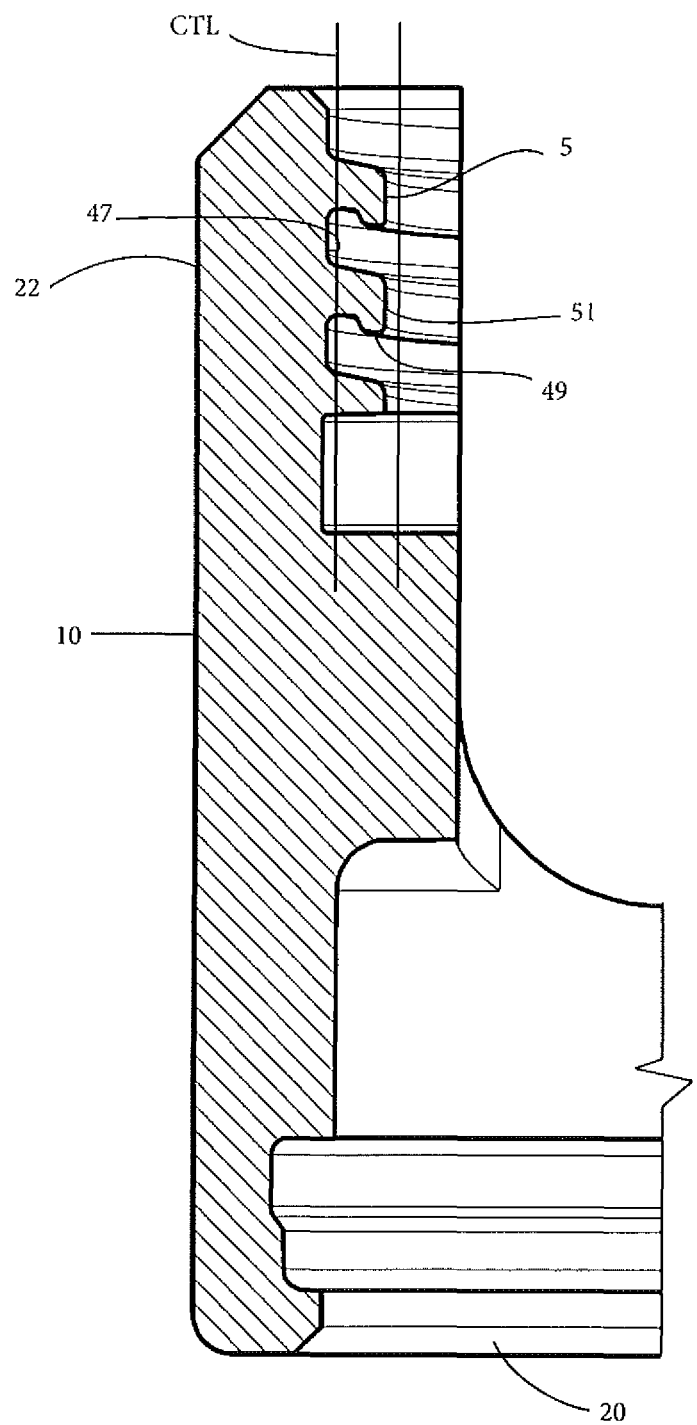
FIG. 6 is an enlarged and partial front elevational view with portions broken away of the receiver of FIG. 1.

With reference to FIG. 6, it is noted that the closure 7 flange form 4 depth D illustrated in FIG. 2 and discussed previously herein is preferably designed by combining both beam (tension) theory and thread theory. It is believed that a larger core diameter (2R1) for the closure 7 and a shorter thread depth D thereof is advantageous in decreasing bending moments on the receiver arms 22. This is because such thread loading flanks are positioned closer to a central tension line CTL (see, e.g., FIG. 6 that shows a theoretical central tension line CTL for the receiver 10) within the upwardly extending arms 22 of the U-shaped receiver 10. Moving the root of the male closure flange form 4 outwardly as close as possible to the theoretical tension line CTL in the receiver 10 arms is desirable in that it can decrease a resultant bending moment on the receiver arms 22. By so doing, the outer diameter of the closure top (2R2) measured between crest surfaces 31 can remain the same size for a given receiver 10.

Figure 7:
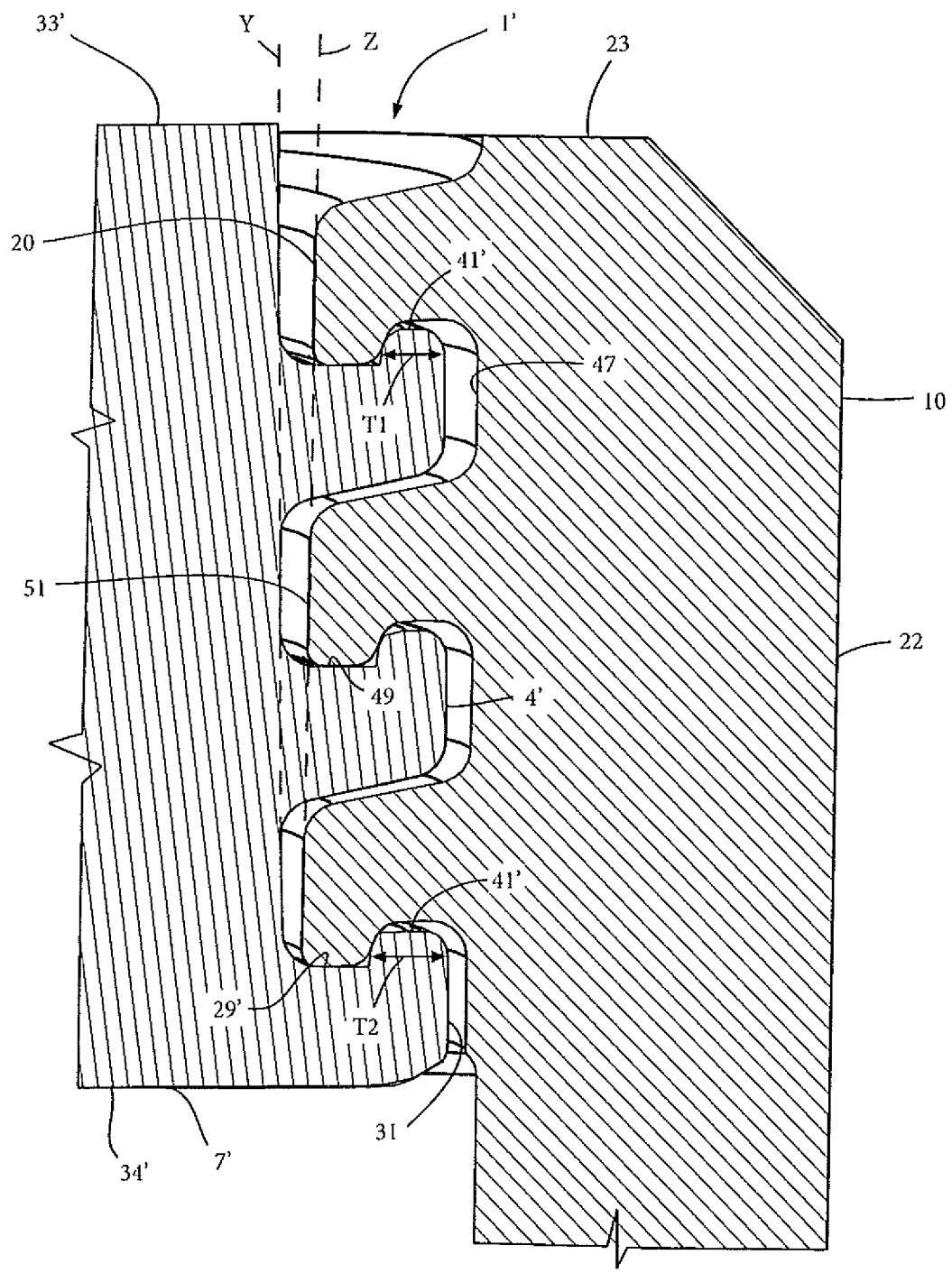
FIG. 7 is an enlarged and partial front elevational view with portions broken away of the receiver of FIG. 1 and shown with an alternative closure, also in partial front elevational view with portions broken away to show the detail thereof.

With reference to FIG. 7, an alternative embodiment of a closure mechanism 1' utilizing an alternative closure 7' with the receiver 10 is shown. The closure 7' is identical to the closure 7 previously described herein with the exception of a radially extending thickness or depth T measured at a toe 41' of the closure flange form 4'. As illustrated in FIG. 7, the thickness T increases gradually from T1 to T2 in a downward spiral direction from a top 33' to a bottom 34' of the closure 7'.

Figure 8:
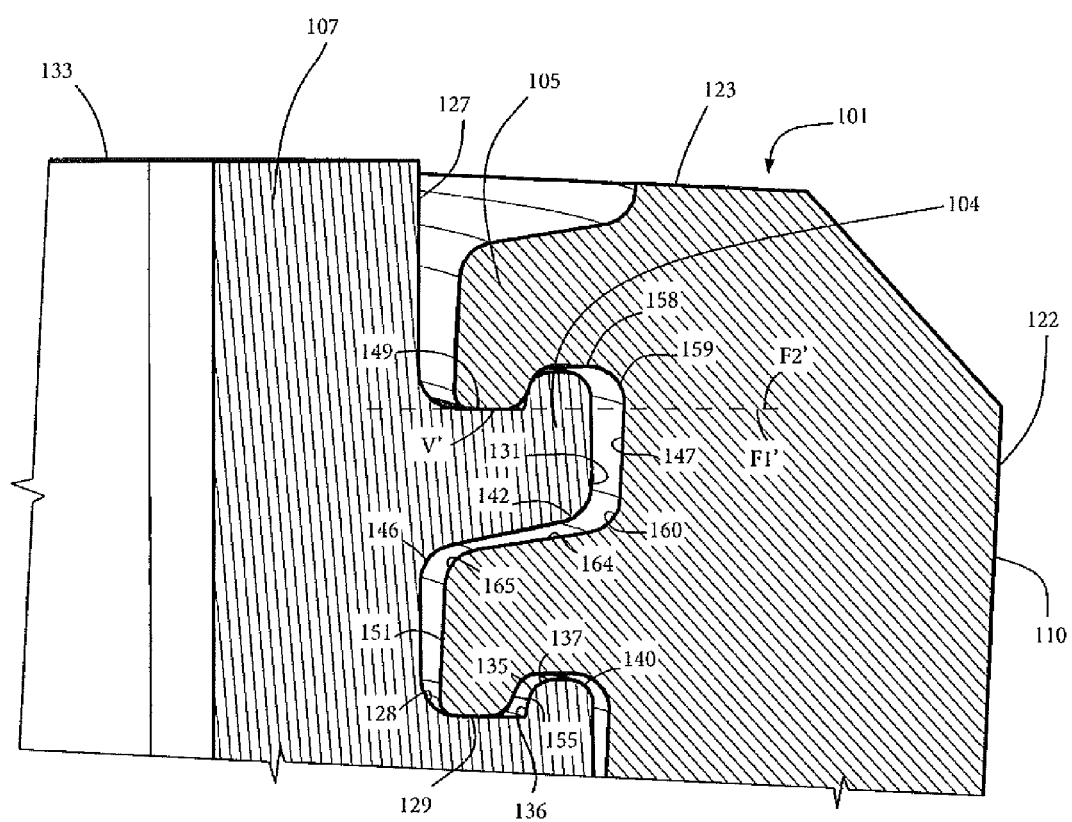
FIG. 8 is a greatly enlarged fragmentary cross sectional view of a first modified embodiment of a spinal implant closure flange form according to the present invention.

With reference to FIG. 8, an alternative embodiment is shown wherein as a closure flangeform 107 is tightened each receiver arm 122 experiences some outward pivot-splay. FIG. 8 shows that upon tightening, contact between the top flange splay control ramps 135 and 155 arrests any further pivot-splay of the receiver arms 122. During the rotating and tightening of the closure 107 within the receiver 110, radially outer portions of both load flanks 129 and 149 engage one another, whereas the other flange toes 141 do not necessarily engage splay control ramps 155. In the illustrated embodiment translation of a contact region or area V' between the load flanks 129 and 149 on the top thread only, after final tightening, and splaying of the receiver arms 122, sequentially in the top flange, both surfaces 129 and 149 would be mating and parallel or flush with one another, such that F1' and F2' are aligned and the angle C' is zero; however, initially the closure loading surface 129 would extend radially in cross section from the closure 107 and the receiver flank surface 149 would initially slope rearwardly in cross section from the crest to the root of the receiver thread 105, preferably the angle rearward being such that the two load surfaces become fully mating and parallel when the closure 107 is fully received in the receiver 110 and fully tightened. It is foreseen that intermediate between the embodiments of FIGS. 7 and 8 could also be utilized.

Figure 9:
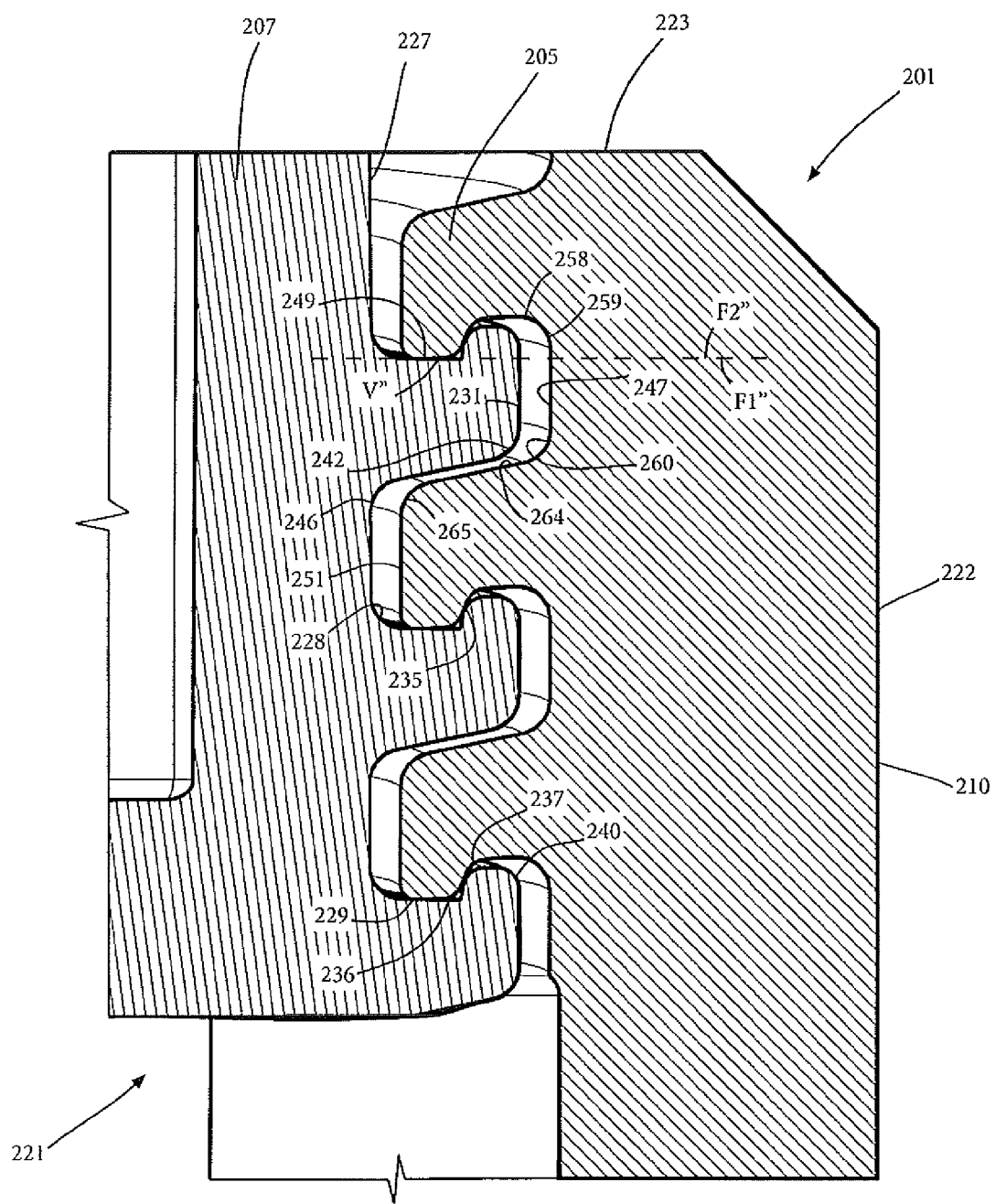
FIG. 9 is a greatly enlarged fragmentary cross sectional view of a second modified embodiment of a spinal implant closure flange form according to the present invention.

With reference to FIG. 9, another alternative embodiment is shown wherein as a closure 207 is tightened each receiver arm 222 experiences some outward pivot-splay. FIG. 9 shows that upon tightening, contact between the splay control ramps 235 and 255 arrests any further pivot-splay of the receiver arms 222 for every tier of the flange form 204 (that is every 360° revolution) sequentially as the flange is tightened and rotated downwardly. During the rotating and tightening of the closure 207 within the receiver 210, radially outer portions of both load flanks 229 and 249 engage one another. In FIG. 9, the contact area or region V''' between the load flanks 229 and 249 on each tier of the flange form 204, after final closure and splaying of the receiver arms 222, mate and are parallel or flush, such that F1" and F2" are aligned and the angle C' is zero; however, initially, each closure loading surface 229 would extend radially in cross section from the closure 207 and each receiver flank surface 249 would initially slope rearwardly in cross section from the crest to the root of the receiver flange 205, preferably the angle rearward is configured so that the two load surfaces become fully mating and parallel in sequence as the closure 207 is fully received in the receiver 210 and fully tightened, as seen in FIG. 7 top flange form. Furthermore, the shape of each tier is slightly different, such that when the closure 207 is fully tightened, the splay control ramps 235 and 255 are in touching relationship or very closely spaced from each other, as compared to the embodiment of FIG. 1, wherein the splay control ramps of only the top tier are in touching or closely spaced relationship to each other and are increasingly spaced with each successive lower tier.

It is to be understood that while certain forms of the present invention have been illustrated and described herein, it is not to be limited to the specific forms or arrangement of parts described and shown.

What is claimed and desired to be secured by Letters Patent is as follows:

1. A spinal fixation structure comprising:
    a closure flange form extending helically about a central axis of a closure;
    a closure load flank of the closure flange form, the closure load flank sloping in a direction radially outwards from a root surface towards an outer crest surface, the closure load flank in a non-parallel relationship with a receiver load flank of a receiver flange form extending helically along an inner surface of a set of upright arms of a receiver; and
    a closure splay control ramp disclosed adjacent the closure load flank, the closure splay control ramp configured to engage a receiver splay control ramp of the receiver flange form, the engagement of the closure flange form and the receiver flange form generating a controlled pivot-splay during rotational mating of the closure within the receiver, the controlled pivot-splay generating an outward pivot having a center of rotation disposed within each of the upright arms and reducing torque of the closure during loading of the closure into the receiver, the controlled pivot-splay arresting the outward pivot of the set of upright arms when the closure is it a locking engagement with the receiver.

* * * * *

UNITED STATES PATENT AND TRADEMARK OFFICE
CERTIFICATE OF CORRECTION

PATENT NO. : 9,717,533 B2
APPLICATION NO. : 14/581165
DATED : August 1, 2017
INVENTOR(S) : Roger P. Jackson et al.

It is certified that error appears in the above-identified patent and that said Letters Patent is hereby corrected as shown below:

In the Claims

- In Claim 1, Column 12, Line 47, delete "it" and insert --in-- therefor.

Signed and Sealed this
Nineteenth Day of December, 2017

Joseph Matal
*Performing the Functions and Duties of the*
*Under Secretary of Commerce for Intellectual Property and*
*Director of the United States Patent and Trademark Office*